(12) United States Patent
Goodrich

(10) Patent No.: US 7,186,543 B1
(45) Date of Patent: Mar. 6, 2007

(54) PREPARATION OF VACCINES USING A PHOTOSENSITIZER AND LIGHT

(75) Inventor: Raymond P. Goodrich, Lakewood, CO (US)

(73) Assignee: Gambro Inc., Lakewood, CO (US)

( * ) Notice: Subject to any disclaimer, the term of this patent is extended or adjusted under 35 U.S.C. 154(b) by 367 days.

(21) Appl. No.: 10/325,402

(22) Filed: Dec. 20, 2002

Related U.S. Application Data

(63) Continuation-in-part of application No. 09/586,147, filed on Jun. 2, 2000, now abandoned, which is a continuation-in-part of application No. 09/357,188, filed on Jul. 20, 1999, now Pat. No. 6,277,337, which is a continuation-in-part of application No. 09/119,666, filed on Jul. 21, 1998, now Pat. No. 6,258,577.

(60) Provisional application No. 60/342,851, filed on Dec. 20, 2001.

(51) Int. Cl.
C12N 7/04 (2006.01)
C12N 7/06 (2006.01)

(52) U.S. Cl. ............................. 435/236; 435/4; 435/5

(58) Field of Classification Search .................... 435/4, 435/5, 173.1, 173.3
See application file for complete search history.

(56) References Cited

U.S. PATENT DOCUMENTS

| | | |
|---|---|---|
| 3,259,546 A | 7/1966 | Polley |
| 4,402,318 A | 9/1983 | Swartz |
| 4,545,987 A | 10/1985 | Giles et al. |
| 4,556,556 A | 12/1985 | Wiesehahn et al. |
| 4,693,981 A | 9/1987 | Wiesehahn et al. |
| 4,915,683 A | 4/1990 | Sieber |
| 4,960,408 A | 10/1990 | Klainer et al. |
| 5,106,619 A | 4/1992 | Wiesehahn et al. |
| 5,143,717 A * | 9/1992 | Davis ........................ 424/45 |
| 5,571,666 A | 11/1996 | Floyd et al. |
| 5,686,436 A | 11/1997 | Van Dyke |
| 5,846,961 A | 12/1998 | Van Dyke |
| 6,165,711 A | 12/2000 | Dorner et al. |
| 6,258,577 B1 | 7/2001 | Goodrich et al. |
| 6,268,120 B1 | 7/2001 | Platz et al. |
| 2004/0005712 A1 | 1/2004 | Platz |
| 2004/0006028 A1 | 1/2004 | Platz |
| 2004/0038373 A1 | 2/2004 | Platz et al. |

FOREIGN PATENT DOCUMENTS

| | | |
|---|---|---|
| EP | 0124363 | 11/1984 |
| EP | 0196515 | 10/1986 |
| WO | WO03/054150 | 7/2003 |
| WO | WO03/095621 | 11/2003 |
| WO | WO2004/043338 | 5/2004 |

OTHER PUBLICATIONS

Eertweigh et al, Adjuvant treatment of colorectal cancer: Towards tumor-specific immunotherapies, *Cancer and Metastasis Reviews*, 20:101-108, 2001.
Vermorken et al, "Active specific immunotherapy for stage II and stage III human colon cancer: a randomized trial", *The Lancet*, 353:345-50, 1999.
Baars et al, A phase II study of active specific immunotherapy and 5-FU/Leucovorin as adjuvant therapy for stage III colon carcinoma, *British Journal of Cancer*, 86(8):1230-1234, 2002.
International Search Report for corresponding foreign application: PCT/US02/40923.
Balladur, Helene, "Photolysis of Riboflavin Induces Apoptosis in Epstein-Barr Virus Transformed Lymphoblastoid Cells: Design of a Cellular Vaccine for EBV-Associate Lymphoma", Masters Thesis, Ohio State University, 2002, pp. 57-65.
Dardare et al, "Binding Affinities of Commonly Employed Sensitizers of Viral Inactivation", *Photochemistry and Photobiology*, 2002, 75(6): 561-564.
Wagner et al, "Determination of Residual 4'-aminomethyl-4,5',8-trimethylpsoralen and Mutagenicity Testing following Psoralen Plus UVA Treatment of Platelet Suspensions", *Photochemistry and Photobiology*, vol. 57, No. 5, pp. 819-824, 1993.
International Search Report for corresponding foreign application: PCT/US02/40923 (2003).

* cited by examiner

*Primary Examiner*—Stacy B. Chen
(74) *Attorney, Agent, or Firm*—Laura B. Arciniegas; Edna M. O'Connor; John R. Merkling

(57) ABSTRACT

Methods are provided for treating a vaccine containing infectious particles which may be viral, bacterial, and/or cellular in nature. Preferred methods include the steps of adding an effective, non-toxic amount of an endogenous photosensitizer to the fluid and exposing the fluid to photoradiation sufficient to inactivate the infectious particles but not enough to damage the antigenic characteristics of the infectious particles.

11 Claims, 22 Drawing Sheets

PREPARATION OF VACCINES USING A PHOTOSENSITIZER AND LIGHT

CROSS REFERENCE TO RELATED APPLICATIONS

This application claims priority from Provisional U.S. Patent Application No. 60/342,851 filed Dec. 20, 2001; and is a continuation-in-part of U.S. patent application Ser. No. 09/586,147 filed Jun. 2, 2000 now abandoned which is a continuation-in-part of U.S. patent application Ser. No. 09/357,188 filed Jul. 20, 1999 now issued as U.S. Pat. No. 6,277,337; which is a continuation-in-part of U.S. patent application Ser. No. 09/119,666 filed Jul. 21, 1998 now issued as U.S. Pat. No. 6,258,577; all of which are incorporated herein in their entirety to the extent not incompatible herewith.

FIELD OF THE INVENTION

The present invention relates to the preparation of vaccines. More particularly, the invention relates to inactivation of infectious particles in a vaccine whether viral, bacterial or cellular in nature. The infectious particles are inactivated using an endogenous photosensitizer and light, under conditions which limit antigenic degradation of the infectious particles in order to elicit an immune response but prevent replication of the infectious particles.

BACKGROUND OF THE INVENTION

Every day, the body is bombarded with bacteria, viruses and other infectious agents. When a person is infected with a disease-causing or infectious agent, the body's immune system attempts to mount a defense against it. When the defense is successful, immunity against the infectious agent results. When the defense is not successful, an infection may result.

In the process of developing immunity to the infectious agent, the B cells of the body produce substances known as antibodies that act against the specific infectious agent and create a "memory" of this experience that can be called upon for protection when exposed to the same infectious agent again months or years later. The next time the person encounters this particular infectious agent, the circulating antibodies quickly recognize it and enable it to be eliminated from the body by other immune cells before signs of disease develop. It is estimated that antibodies which can recognize over 10,000 different antigens or foreign (non-self) infectious agents are circulating in the blood stream.

A vaccine works in a similar way in that it produces an immunogenic response. However, instead of initially suffering the natural infection and risking illness in order to develop this protective immunity, vaccines create a similar protective immunity without exposing the body to the disease.

Development of vaccines against both bacterial and viral diseases has been one of the major accomplishments in medicine over the past century. While effective vaccines have been developed for a large number of diseases, the need for development of safe and effective vaccines for a number of additional diseases remains.

Several basic strategies are used to make vaccines. One strategy is directed toward preventing viral diseases by weakening or attenuating a virus so that the virus reproduces very poorly once inside the body. Measles, mumps, rubella (German measles) and chickenpox (varicella) vaccines are made this way. Whereas natural viruses usually cause disease by reproducing themselves many thousands of times, weakened vaccine viruses reproduce themselves approximately 20 times. Such a low rate of replication is generally not enough to cause disease. Although the preparation of live, attenuated infectious agents as vaccines will often provide improved immunologic reactivity, such methods do increase the risk that the vaccine itself will be the cause of infection, and that the attenuated organism will propagate and provide a reservoir for future infection. One or two doses of live "weakened" viruses may provide immunity that is life long; however, such vaccines cannot be given to people with weakened immune systems.

Another way to make viral vaccines is to inactivate the virus. By this method, viruses are completely inactivated or killed using a chemical. Killing the virus makes the virus unable to replicate in a body and cause disease. Polio, hepatitis A, influenza and rabies vaccines are made this way. The use of inactivated or killed bacterial or viral agents as a vaccine used to induce an immunogenic response, although generally safe, will not always be effective if the immunogenic characteristics of the agent are altered. An inactive virus can be given to people with weakened immune systems, but must be given multiple times to achieve immunity.

Vaccines may also be made using parts of the virus. With this strategy, a portion of the virus is removed and used as a vaccine. The body is able to recognize the whole virus based on initial exposure to a portion of the virus. The hepatitis B vaccine for example, is composed of a protein that resides on the surface of the hepatitis B virus.

Vaccines are also made to help combat diseases caused by bacteria. Several bacterial vaccines are made by taking the toxins produced by bacteria and inactivating them using chemicals. By inactivating the toxins, the bacteria no longer causes disease. Diphtheria, tetanus and pertussis vaccines are made this way. Another strategy to make bacterial vaccines is to use part of the sugar coating (or polysaccharide) of the bacteria to induce the immunogenic response. Protection against certain bacteria are based on responsive immunity to this sugar coating.

Thus, one must generally choose between improved effectiveness or greater degree of safety when selecting between the inactivation and attenuation techniques for vaccine preparation. The choice is particularly difficult when the infectious agent is resistant to inactivation and requires highly rigorous inactivation conditions which are likely to degrade the antigenic characteristics which help to induce an immune response and provide subsequent immunity.

In addition to the dead or weakened infectious agent, vaccines usually contain sterile water or saline. Some vaccines are prepared with a preservative or antibiotic to prevent bacterial growth. Vaccines may also be prepared with stabilizers to help the vaccine maintain its effectiveness during storage. Other components may include an adjuvant which helps stimulate the production of antibodies against the vaccine to make it more effective.

Methods to prepare vaccines today involve treating samples with glutaraldehyde or formaldehyde to fix or cross-link the cells or infectious particles. Such treatments generally involve denaturation of the native forms of the infectious particles. A disadvantage to this approach is that the protein coats of the infectious particles are damaged by this process, and thus may not be recognized by the immune system.

Therefore, the need exists for a method to prepare vaccines that are recognized by the immune system but do not replicate once inside the body.

The use of photosensitizers, compounds which absorb light of a defined wavelength and transfer the absorbed energy to an energy acceptor, are known to be useful in the sterilization of blood components. For example, European Patent application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red, and methylene blue, as blood additives. Protoporphyrin, which occurs naturally within the body, can be metabolized to form a photosensitizer; however, its usefulness is limited in that it degrades desired biological activities of proteins. Chlorpromazine, is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. No. 5,607,924 issued Mar. 4, 1997 and U.S. Pat. No. 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The reactivity of psoralen derivatives with viruses has been studied. See, Hearst and Thiry (1977) Nuc. Acids Res. 4:1339–1347; and Talib and Banerjee (1982) Virology 118:430–438. U.S. Pat. Nos. 4,124,598 and 4,196,281 to Hearst et al. suggest the use of psoralen derivatives to inactivate RNA viruses, but include no discussion of the suitability of such inactivated viruses as vaccines. U.S. Pat. No. 4,169,204 to Hearst et al. suggests that psoralens may provide a means for inactivating viruses for the purpose of vaccine production but presents no experimental support for this proposition. European patent application 0 066 886 by Kronenberg teaches the use of psoralen inactivated cells, such as virus-infected mammalian cells, for use as immunological reagents and vaccines. Hanson (1983) in: Medical Virology II, de la Maza and Peterson, eds., Elsevier Biomedical, New York, pp. 45–79, reports studies which have suggested that oxidative photoreactions between psoralens and proteins may occur. Wiesehahn et al. discloses in U.S. Pat. Nos. 4,693,981 and 5,106,619 the use of psoralens to prepare inactivated viral vaccines. These patents disclose preparing vaccines by treating viruses with furocoumarins and long wavelength UV light for a time period sufficiently long enough to render the virus non-infectious but less than that which would result in degradation of its antigenic characteristics under conditions which limit the availability of oxygen and other oxidizing species. Swartz discloses in U.S. Pat. No. 4,402,318 a method of producing a vaccine by adding methylene blue and exposing the vaccine to light and an electric field concurrently to completely inactivate the viruses, bacteria, cells and toxins. Dorner et al. in U.S. Pat. No. 6,165,711 discloses a process for disintegrating nucleic acids to make vaccines by exposing biologically active material to phenothiazine and a laser beam.

The mechanism of action of psoralens is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of psoralens is that they attack cell membranes of desirable components of fluids to be decontaminated, such as red blood cells, and the singlet oxygen produced during the reaction also attacks desired protein components of fluids being treated.

U.S. Pat. No. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued Jun. 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses this problem of prevention of damage to other blood components.

Photosensitizers which attack nucleic acids are known to the art. U.S. Pat. No. 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. This patent fails to disclose an apparatus for decontaminating blood on a flow-through basis. U.S. Pat. No. 5,798,238 to Goodrich, Jr., et al., discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin (7,8-dimethyl-10-ribityl isoalloxazine) has been reported to attack nucleic acids. U.S. Pat. Nos. 6,258,577 and 6,277,337 issued to Goodrich et al. disclose the use of riboflavin and light to inactivate microorganisms which may be contained in blood or blood products. U.S. Pat. No. 6,268,120 to Platz et al. discloses riboflavin derivatives which may be used to inactivate microorganisms.

SUMMARY OF THE INVENTION

It is one aspect of the instant invention to provide improved methods for inactivating infectious particles, which methods are capable of inactivating even the most resistant particles under conditions which do not substantially degrade the antigenic structure of the particles. In particular, the inactivated infectious particles should be useful as vaccines and free from adverse side effects at the time of administration as well as upon subsequent challenge with the live infectious agents upon future exposure.

One method for inactivating infectious particles without substantially degrading the antigenic characteristics of the particles, may include the steps of exposing the infectious particles to an inactivation fluid containing at least an endogenous photosensitizer in an amount sufficient to render the particles substantially non-infectious; and exposing the infectious particles and inactivation fluid to light of a sufficient wavelength to render the particles substantially non-infectious but less than that which would result in degradation of the antigenic characteristics of the infectious particles.

The particles are rendered substantially non-infectious by damaging the nucleic acids of the infectious particles, preventing the particles from replicating one inside the recipient of the vaccine.

DETAILED DESCRIPTION

Figure 1:
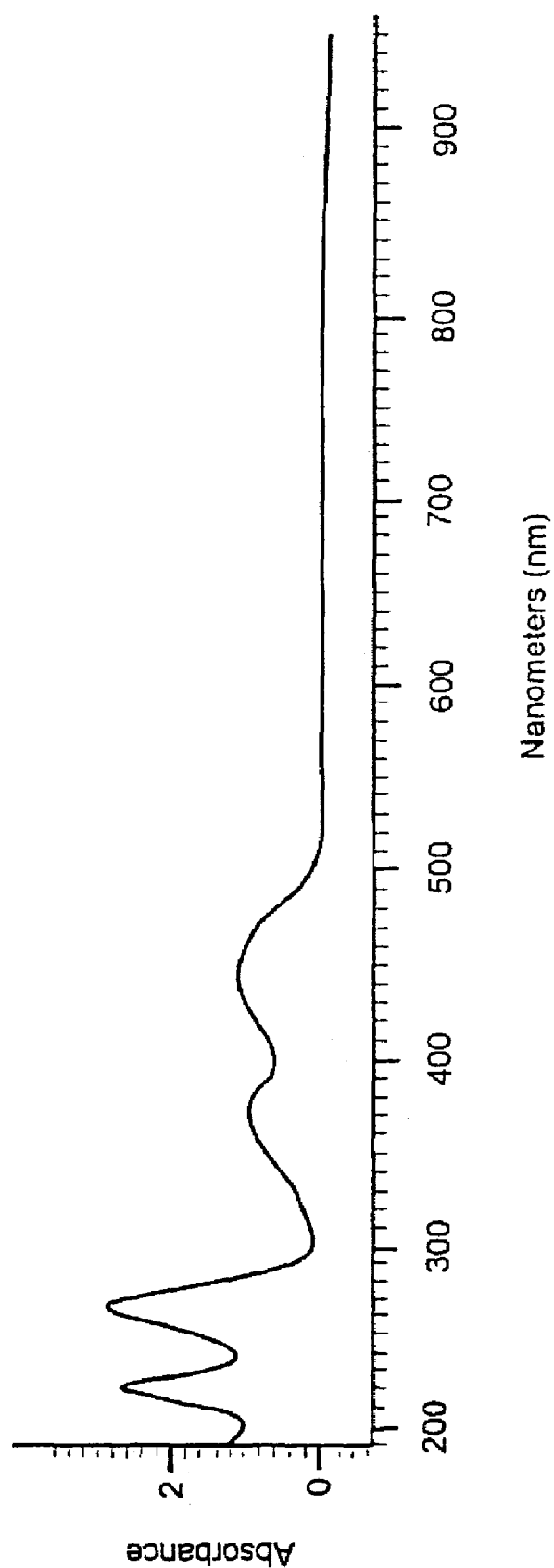
FIG. 1 depicts the riboflavin absorbance spectrum.

According to the present invention, vaccines useful for the inoculation of mammalian hosts, including both animals and humans, against infection are provided. The vaccines may be prepared by inactivation of infectious particles in an inactivation medium containing an amount of an inactivating endogenous photosensitizer or endogenous photosensitizer derivative sufficient to inactivate the infectious particles upon subsequent irradiation. Degradation of the antigenic characteristics of the infectious particles are reduced or eliminated by use of an endogenous photosensitizer, and in particular an isoalloxazine or isoalloxazine derivative. Suitable vaccines may be prepared by combining the inactivated infectious particles with a physiologically-acceptable carrier, such as water, saline or an adjuvant, in an appropriate amount to elicit an immune response, e.g., the production of serum neutralizing antibodies, upon subsequent inoculation of the host.

As used herein, the term "inactivation of an infectious particle" or "agent" means substantially preventing the infectious particle or agent from replicating, either by killing the particles or otherwise interfering with its ability to reproduce, while still maintaining the antigenic characteristics of the particles.

Decontamination methods of this invention using endogenous photosensitizers or endogenously-based photosensitizer derivatives do not substantially destroy the antigenicity on the surface of the infectious particles but do substantially destroy the nucleic acids of the particles and therefore the replicative ability of the particles. So long as the infectious particles retain sufficient antigenic determination to be useful for their intended purpose of inducing immunity in a mammal, their biological activities are not considered to be "substantially destroyed."

Infectious particles or agents which may be present in a vaccine include viruses (both extracellular and intracellular), bacteria, bacteriophages, fungi, blood-transmitted parasites, protozoa, virus infected cells, cancer cells, dendritic cells or altered immune cells. Exemplary viruses which may be made into vaccines include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, adenovirus, papovaviruses, poxviruses, picornavirus, paramyoxovirus, coronavirus, calicivirus, togavirus, rhabdovirus and others known to the art.

Bacteriophages include $\Phi$X174, $\Phi$6, $\lambda$, R17, $T_4$, and $T_2$.

Exemplary bacteria may include but not be limited to *P. aeruginosa, S. aureus, S. epidermidis, L. monocytogenes, E. coli, K pneumonia, S. marcesoens, E. faecalis, B. subtilis, S. pneumoniae, S. pyogenes, S. viridans, B. cereus, E. aerogenes, Propionabacter, K. pneumoniae, C. perfringes, E. cloacae, P. mirabilis, S. cholerasuis, S. liquifaciens, S. mitis, Y. enterocolitica, P. fluorescens, S. enteritidis, C. freundii.*

Exemplary cells which may be used to make vaccines include tumor cells, virus infected cells and immune cells which may include dendritic cells and T and B cells.

Materials which may be treated by the methods of this invention include any materials or components of vaccines which are adequately permeable to photoradiation to provide sufficient light to achieve inactivation of the infectious particles, or which can be suspended or dissolved in fluids which have such permeability to photoradiation. Examples of such materials may be the infectious particle and/or any components or compositions included in vaccine preparations such as adjuvants, antibiotics, preservatives, stabilizers, saline and/or water. The infectious particles which may be used in a vaccine may be used in whole (the entire infectious particle) or portions of the particle (such as the protein coat of a virus) may be used.

The term "biologically active" means capable of effecting a change in a living organism or component thereof. Similarly, "non-toxic" with respect to the photosensitizers means low or no toxicity to humans and other mammals, and does not mean non-toxic to the particles being inactivated. "Substantial destruction" of biological activity means at least as much destruction as is caused by porphyrin and porphyrin derivatives, metabolites and precursors which are known to have a damaging effect on biologically active proteins and cells of humans and mammals.

Similarly, "substantially non-toxic" means less toxic than porphyrin, porphyrin derivatives, metabolites and precursors.

The photosensitizers useful in this invention include any photosensitizers known to the art to be useful for inactivating microorganisms or other infectious particles. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous photosensitizers are used, particularly when such photosensitizers are not inherently toxic or do not yield toxic photoproducts after photoradiation, no removal or purification step is required after decontamination, and treated product can be directly administered to a patient by any methods known in the art. Preferred endogenous photosensitizers are:

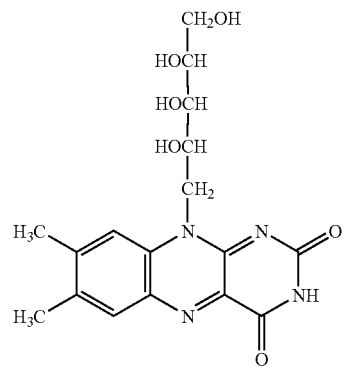

7,8-dimethyl-10-ribityl isoalloxazine

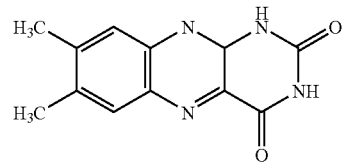

7,8-dimethylalloxazine

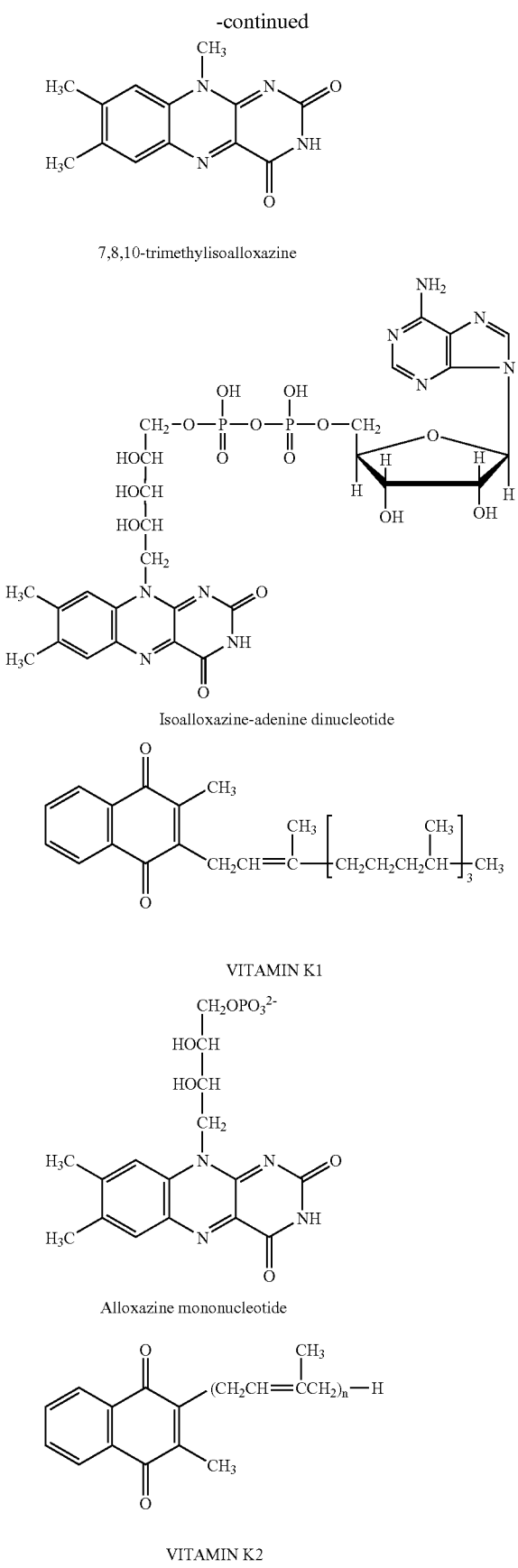
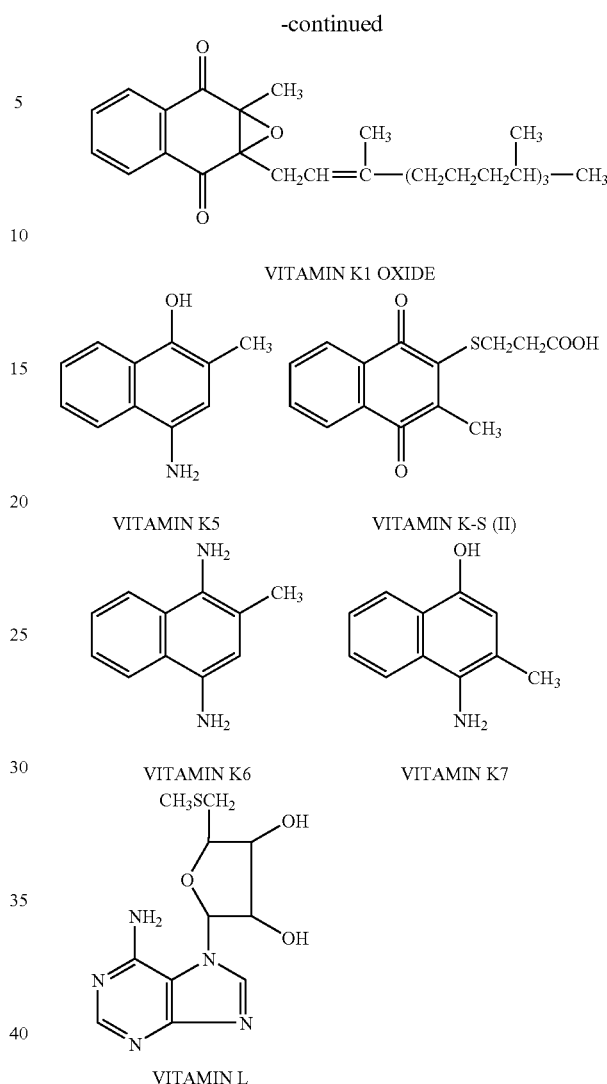

The method of this invention requires mixing the photosensitizer with the material to be decontaminated. In this particular application, the preferred material or fluid is one containing infectious particles from which it is desired to make a vaccine. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. A mixing step may optionally be added. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate the reproductive ability of an infectious particle, but in many embodiments, still maintain the antigenic properties necessary to induce an immune reaction in a mammal and produce subsequent immunity. As taught herein, optimal concentrations for desired photosensitizers may be readily determined by those skilled in the art without undue experimentation. Preferably the photosensitizer is used in a concentration of at least about 1 µM up to the solubility of the photosensitizer in the fluid, and preferably about 10 µM. For 7,8-dimethyl-10-ribityl isoalloxazine a concentration range between about 1 µM and about 160 µM is preferred, preferably about 10 µM.

The fluid containing the photosensitizer is exposed to photoradiation of the appropriate wavelength to activate the photosensitizer, using an amount of photoradiation sufficient to activate the photosensitizer as described above, but less than that which would cause damage to the antigenic determinants of the infectious particles and render the inactivated infectious particle unable to induce an immune response in a mammal. The wavelength used will depend on the photosensitizer selected, as is known to the art or readily determinable without undue experimentation following the teachings hereof. Preferably the light source is a fluorescent or luminescent source providing light of about 300 nm to about 700 nm, and more preferably about 320 nm to about 447 nm of radiation. Wavelengths in the ultraviolet to visible range are useful in this invention. The light source or sources may provide light in the visible range, light in the ultraviolet range, or may be a mixture of light in the visible and ultraviolet ranges.

The activated photosensitizer is capable of inactivating the infectious particles present, such as by interfering to prevent their replication. Specificity of action of the photosensitizer is conferred by the close proximity of the photosensitizer to the nucleic acid of the particle and this may result from binding of the photosensitizer to the nucleic acid. "Nucleic acid" includes ribonucleic acid (RNA) and deoxyribonucleic acid (DNA). Other photosensitizers may act by binding to cell membranes or by other mechanisms. The photosensitizer may also be targeted to the particles to be inactivated by covalently coupling to an antibody, preferably a specific monoclonal antibody to the particle.

The fluid containing the photosensitizer may be flowed into a photopermeable container for irradiation. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ and Spectra™ apheresis systems of GambroBCT, Inc., have been used to exemplify another embodiment involving batch-wise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosensitizer molecules at all distances from the light source and ensure inactivation of infectious particles in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings hereof, and together with the flow rate of fluid through the container, the intensity of the photoradiation and the absorptivities of the fluid components, will determine the amount of time the fluid needs to be exposed to photoradiation. For 7,8-dimethyl-10-ribityl isoalloxazine, a preferred amount of radiation is between about 1 $J/cm^2$ to 120 $J/cm^2$.

In another embodiment involving batch-wise treatment, the fluid to be treated is placed in a photopermeable container which is agitated and exposed to photoradiation for a time sufficient to substantially inactivate the infectious particles, but not enough to destroy the antigenicity of the particles. The photopermeable container is preferably a blood bag made of transparent or semitransparent plastic, and the agitating means is preferably a shaker table. The photosensitizer may be added to the container in powdered or liquid form and the container agitated to mix the photosensitizer with the fluid and to adequately expose all the fluid to the photoradiation to ensure inactivation of the particles.

Photosensitizer may be added to or flowed into the photopermeable container containing the infectious particles to be inactivated. In one embodiment, the photosensitizer is added to the fluid which is used to suspend the inactivated infectious particles to create the vaccine. In another embodiment, the photosensitizer may be added to the infectious particles to be inactivated and the suspension fluid or carrier fluid.

Enhancers may also be added to the fluid to make the process more efficient and selective. Such enhancers include antioxidants or other agents to prevent damage to desired fluid components or to improve the rate of inactivation of infectious particles and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof.

This invention may also comprise fluids comprising biologically active protein, which may be used to produce passive immunity in a patient. Passive immunity involves administration of antibodies such as immunoglobins which may be injected into patients to provide short-term protection to those individuals who have been or will be exposed to a specific pathogen and is typically used in immunocompromised patients who are unable to produce an effective immune response with active immunization. Fluids containing biologically active proteins and also containing endogenous photosensitizer, endogenously-based derivative photosensitizer, or photoproduct thereof may be injected into a patient to provide such passive immunity. The fluid may also contain inactivated microorganisms.

In decontamination systems of this invention, the photoradiation source may be connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., especially when the amount of fluid exposed to the light is small, which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Preferably, the temperature is kept between about 0° C. and about 45° C., more preferably between about 4° C. and about 37° C., and most preferably about 22° C.

The photoradiation source may be a simple lamp or may consist of multiple lamps radiating at differing wavelengths. The photoradiation source should be capable of delivering from about 1 to at least about 120 J/cm$^2$. The use of mixed ultraviolet and visible light is especially preferred when the photosensitizer is one which loses its capacity to absorb visible light after a period of exposure, such as 7,8-dimethyl-10-ribityl-isoalloxazine.

Any means for adding the photosensitizer to the fluid to be decontaminated and for placing the fluid in the photopermeable container known to the art may be used, such means typically including flow conduits, ports, reservoirs, valves, and the like.

For endogenous photosensitizers and derivatives having sugar moieties, the pH of the solution is preferably kept low enough, as is known to the art, to prevent detachment of the sugar moiety. Preferably the photosensitizer is added to the fluid to be decontaminated in a pre-mixed aqueous solution, e.g., in water, storage buffer or suspension solution.

The photopermeable container for the flow-through system may be a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

Decontamination systems as described above may be designed as stand-alone units or may be easily incorporated into existing apparatuses known to the art for inactivating infectious particles to make vaccines.

The use of endogenous photosensitizers and endogenously-based derivative photosensitizers to inactivate infectious particles in vaccines as disclosed herein is described with reference to the inactivation of microorganisms in blood, separated blood components and other cellular components.

Solutions for suspension of the inactivated infectious particles comprising endogenous photosensitizers and endogenously-based derivative photosensitizers as described above are also provided herein. Such suspension or additive solutions may contain physiological saline solution, water, antibiotics, preservatives, stabilizers and adjuvants. The pH of such solutions is preferably between about 7.0 and 7.4. These solutions are useful as carriers for inactivated infectious particles to allow maintenance of quality and viability of the inactivated infectious particles during storage. The photosensitizer may be present in such solutions at any desired concentration from about 1 μM to the solubility of the photosensitizer in the solution, and preferably between about 10 μM and about 100 μM, more preferably about 10 μM. In a preferred embodiment, the suspension solution also comprises enhancers as described above.

The present invention is suitable for producing vaccines to a wide variety of viruses, including human viruses and animal viruses, such as canine, feline, bovine, porcine, equine, and ovine viruses. The method is suitable for inactivating double stranded DNA viruses, single-stranded DNA viruses, double-stranded RNA viruses, and single-stranded RNA viruses, including both enveloped and non-enveloped viruses. The following list contains some representative viruses which may be inactivated by the method of the present invention.

| Viruses which may be inactivated | Representative Viruses |
|---|---|
| dsDNA | |
| Adenoviruses | Adenovirus, canine adenovirus 2 |
| Herpesviruses | Herpes simplex viruses, Feline Herpes I |
| Papovaviruses | Polyoma, Papilloma Poxviruses, Vaccinia |
| ssDNA | |
| Parvovirus | Canine parvovirus, Feline panleukopenia |
| dsRNA | |
| Orbiviruses | Bluetongue virus |
| Reoviruses | Reovirus |
| ssRNA | |
| Calicivirus | Feline calicivirus |
| Coronavirus | Feline infectious peritonitis |
| Myxovirus | Influenza virus |
| Paramyxovirus | Measles virus, Mumps virus, Newcastle disease virus, Canine distemper virus, Canine parainfluenza 2 virus |
| Picornavirus | Polio virus, Foot and mouth disease virus |
| Retrovirus | Feline leukemia virus, Human T-cell lymphoma virus, types I, II and III |
| Rhabdovirus | Vesicular stomatitis virus, rabies |
| Togavirus | Yellow fever virus, Sindbis virus, Encephalitis virus |

Of particular interest are those viruses for which conventional vaccine approaches have been unsuccessful or marginally successful. For such viruses, inactivation procedures which are sufficiently rigorous to assure the total loss of infectivity often result in partial or complete destruction of the antigenic characteristics of the virus. With such loss of antigenic characteristics, the viruses are incapable of eliciting a protective immunity when administered to a susceptible host. While it would be possible to utilize less rigorous inactivation conditions in order to preserve the antigenic integrity of the virus, this approach is not desirable since it can result in incomplete inactivation of the virus, and increase the potential threat of infection of the recipient by the incompletely inactivated virus.

The methods of this invention may also be used to produce vaccines from bacteria or portions of bacteria. Some bacteria which may be used to produce vaccines include but are not limited to diphtheria, tetanus, pertussis, *haemophilus influenzae B, pneumococcus, vibrio cholerae, salmonella typhi* and *neisseria meningiditis*.

Vaccines may be made to treat insect-borne diseases including but not limited to typhus, malaria, dengue fever, yellow fever, chagus babesin, *rickettsia* and west nile virus using the methods of this invention.

Vaccines and methods to produce vaccines from inactivated cancer cells are also contemplated by this invention. For example, vaccines may be made of autologous tumor cells to elicit a long-term anti-tumor immune response, known as active specific immunotherapy. A tumor may be surgically resected from a patient and the tumor cells purified using any method known in the art. One such method to prepare autologous tumor vaccines which may be used in this invention is described in Hanna et al. (Hanna M G Jr, Brandhorst J S, Peters L C, Specific immunotherapy of established visceral micrometastases by BCG-tumour cell vaccine alone or as an adjunct to surgery. *Cancer* 1978; 42: 2613–25) and Peters et al. (Peters L C, Brandhorst J S, Hanna M G Jr., Preparation of immunotherapeutic autologous vaccines form solid tumors. *Cancer Res* 1979; 39: 1353–60) which are both herein incorporated by reference in their entireties to the amount not inconsistent herewith. The purified tumor cells may then be treated with an amount of endogenous photosensitizer and light sufficient to prevent the nucleic acid of the tumor cells from replicating but not enough to damage the antigenic determinants on the surface of the tumor cells. Once the tumor cells have been inactivated, they may be immediately injected back into the patient, or may be frozen for future use.

One method which may be used to make a vaccine for preventing the replication of live tumor cells in a mammal include the removal of a tumor from a mammal having a tumor; purifying at least some of the tumor cells from the tumor; inactivating the tumor cells by exposing the tumor cells to an endogenous photosensitizer and light at a sufficient wavelength to prevent replication of the tumor cells but not substantially destroy the antigenic determinants of the tumor cells; and suspending the inactivated tumor cells in a suspension solution. The photosensitizer may include riboflavin, lumiflavin, lumichrome, napthquinones, napthels and napthalenes, but any photosensitizer which prevents the replication of the tumor cells but does not substantially destroy the antigenic determinants of the cells may be used. The suspension solution may be any solution known in the art.

To inactivate infectious particles in a vaccine, a photosensitizer may be added to the infectious particles and exposed to light of an appropriate wavelength to inactivate the infectious particles while retaining the antigenic properties of the particles before suspension in a sterile physiologically acceptable medium. Alternatively, a photosensitizer may be added after the addition of the medium. The infectious particles are irradiated after the addition of the photosensitizer.

The inactivated infectious particles may be formulated in a variety of ways for use as a vaccine. The concentration of the infectious particles in the vaccine will be in an amount sufficient to induce the production of antibodies by the body in order to provide long-term immunity as is known by those skilled in the art. The vaccine may include cells or may be cell-free. The vaccine may also contain portions of infectious particles. The inactivated infectious particles may be resuspended in an inert physiologically acceptable medium, such as ionized water, phosphate-buffered saline, saline, or the like, or may be administered in combination with a physiologically acceptable immunologic adjuvant, including but not limited to mineral oils, vegetable oils, mineral salts such as aluminum and immunopotentiators, such as muramyl dipeptide. A stabilizer may also be added to help the vaccine maintain its effectiveness during storage. The vaccine may be administered subcutaneously, intramuscularly, intraperitoneally, orally, or nasally. Usually, a total specific dosage at a specific site will range from about 0.1 ml to 4 ml, where the total dosage will range from about 0.5 ml to 8 ml. The number of injections and their temporal spacing may be highly variable, and will depend on the effectiveness of the vaccine and how well the recipients' immune system responds to the vaccine.

It should be noted that any contaminating microorganisms in a pre-existing vaccine made by any known methods may be inactivated as taught by the methods of this invention.

The following examples are offered by way of illustration, not by way of limitation. The below examples show that blood cells contaminated with pathogens which have been treated by the methods of this invention retain their biological activity while the amount of pathogens are substantially reduced. After treatment with photosensitizer and light, infectious particles to be used as a vaccine retain their antigenicity but are unable to replicate.

The decontamination method of this invention using endogenous photosensitizers and endogenously-based derivative photosensitizers is exemplified herein using 7,8-dimethyl-10-ribityl isoalloxazine as the photosensitizer, however, any photosensitizer may be used which is capable of being activated by photoradiation to cause inactivation of infectious particles. The photosensitizer must be one which does not destroy desired components of the fluid being decontaminated, and also preferably which does not break down as a result of the photoradiation into products which significantly destroy desired components or have significant toxicity. The wavelength at which the photosensitizer is activated is determined as described herein, using literature sources or direct measurement. Its solubility in the fluid to be decontaminated or in a combination of carrier fluid and fluid to be contaminated is also so determined. The ability of photoradiation at the activating wavelength to penetrate the fluid to be decontaminated must also be determined as taught herein. Appropriate temperatures for the reaction of the photosensitizer with its substrate are determined, as well as the ranges of temperature, photoradiation intensity and duration, and photosensitizer concentration which will optimize microbial inactivation and minimize damage to desired proteins and/or cellular components in the fluid. Examples 1–7 and FIGS. 1–5 illustrate the determination of information required to develop a flow-through decontamination system of this invention.

Figure 6:
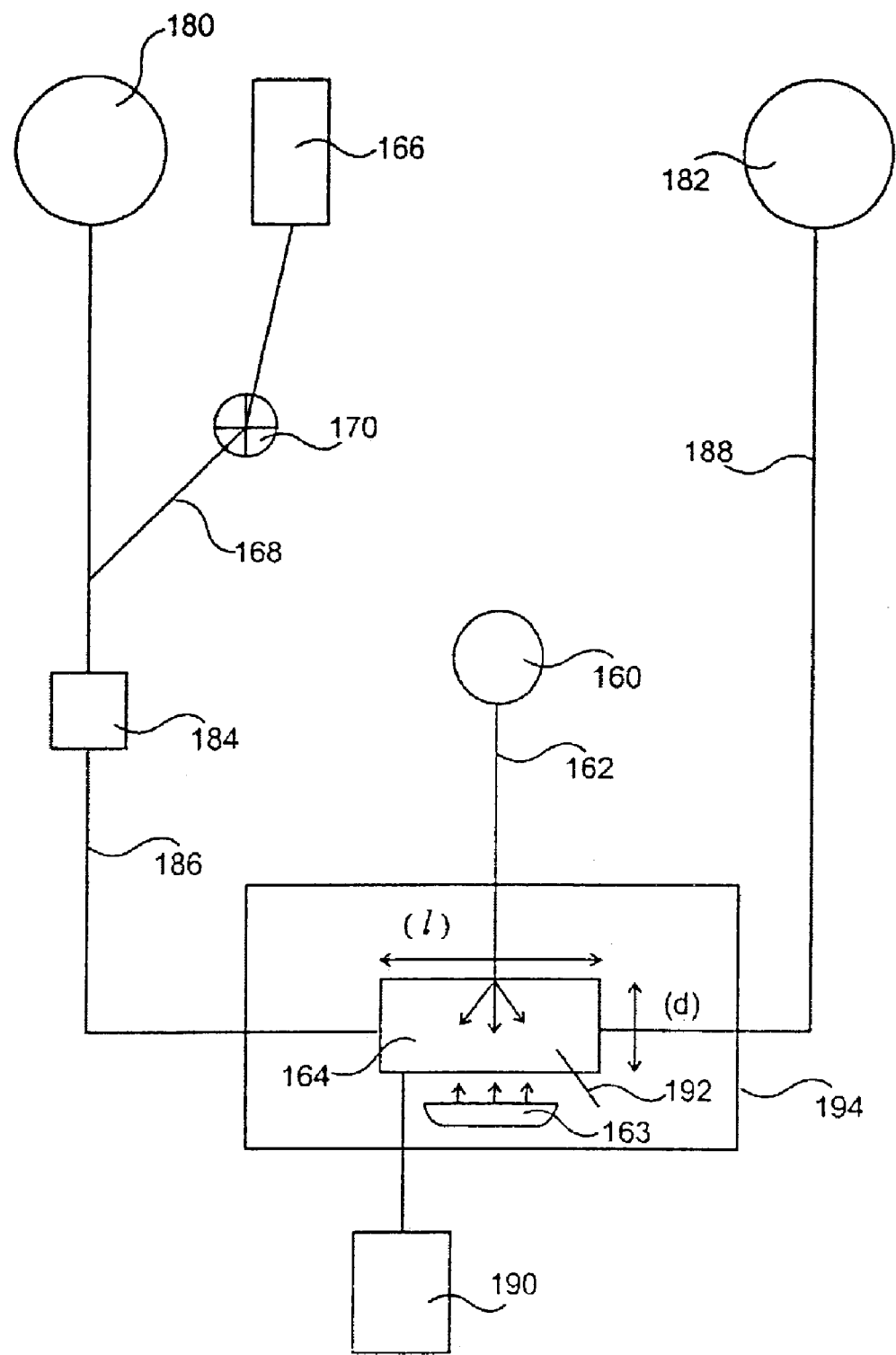
FIG. 6 depicts the decontamination assembly of this invention.

Once such system requirements have been determined for flow-through systems, apparatuses may be designed which provide the correct flow rates, photopermeabilities, and light intensities to cause inactivation of microorganisms present in the fluid, as is taught herein. The fluid to be decontaminated is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopenmeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature. FIG. 6 depicts a decontamination system of this invention as part of an apparatus for separating blood components, and FIG. 7 provides details of a preferred decontamination system.

For batch systems, it is preferred to place the fluid to be decontaminated along with the photosensitizer in bags which are photopermeable or at least sufficiently photopermeable to allow sufficient radiation to reach their contents to activate the photosensitizer. Sufficient photosensitizer is added to each bag to provide inactivation, preferably to provide a photosensitizer concentration of at least about 10 µM, and the bag is agitated while irradiating, preferably at about 1 to about 120 J/cm$^2$ for a period of between about 6 and about 36 minutes to ensure exposure of substantially all the fluid to radiation. Preferably, a combination of visible light and ultraviolet light is used concurrently. The photosensitizer may be added in powdered form.

The method preferably uses endogenous photosensitizers, including endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate the effects of 7,8-dimethyl-10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8-dimethyl-10-ribityl isoalloxazine allows greater selectivity in its action than is the case with compounds such as psoralens which possess significant Type II chemistry.

Figure 7:
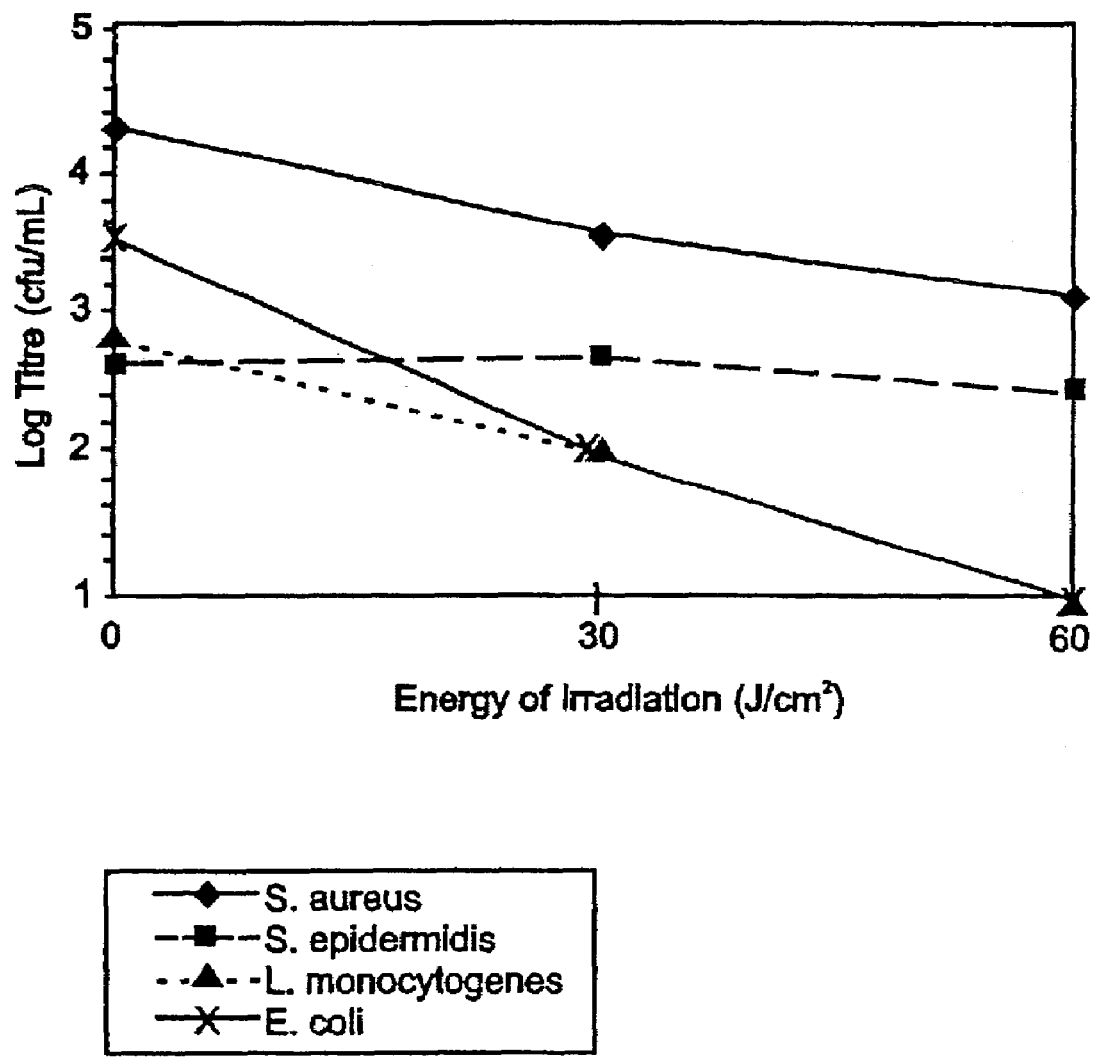
FIG. 7 depicts inactivation of bacteria in platelet preparations using vitamin K5 as the photosensitizer as a function of energy of irradiation.

FIG. 7 depicts a stand-alone version of the decontamination assembly of this invention. The vaccine product containing infectious particles to be inactivated (hereinafter referred to as the product) 180 is connected to product line 186 which leads through pump 184 to decontamination cuvette 164. Photosensitizer reservoir 166 is connected to photosensitizer input line 168 equipped with input pump 170, and leads into product line 186 upstream from decontamination cuvette 164. Decontamination cuvette 164 is a photopermeable cuvette of a depth (d) and a length (l) selected to ensure decontamination. Cooling system 190 combined with temperature monitor 192 are connected with decontamination cuvette 164 for controlling the temperature of the fluid. Decontamination cuvette 164 is connected via light guide 162 to photoradiation source 160. A photoradiation enhancer 163 is placed adjacent to (either touching or spaced apart from) decontamination cuvette 164 to increase the amount of photoradiation reaching the blood product in the cuvette. Decontaminated product line 188 leads from decontamination cuvette 164 to decontaminated product collection 182.

In operation, product 180 is conducted into product line 186 where it is joined by photosensitizer from photosensitizer reservoir 166 flowing at a rate controlled by photosensitizer input pump 170 in photosensitizer input line 68 which joins product line 186. The flow rate in product line 186 is controlled by pump 184 to a rate selected to ensure decontamination in decontamination cuvette 164. Temperature monitor 192 measures the temperature of fluid in cuvette 164 and controls cooling system 190 which keeps the temperature in the cuvette within a range required for optimal operation. The product in decontamination cuvette 164 is irradiated by photoradiation from photoradiation source 160 conducted in light guide 162. The photoradiation source may comprise two or more actual lights. The arrows indicate photoradiation from the end of light guide 162 propagating in the product inside transparent decontamination cuvette 164. Adjacent to decontamination cuvette 164 is photoradiation enhancer 163 which may be an additional source of photoradiation or a reflective surface. The arrows from photoradiation enhancer 163 pointing toward decontamination cuvette 164 indicate photoradiation from photoradiation enhancer 163 shining on the product material in cuvette 164. Decontaminated product exits decontamination cuvette 164 via decontaminated product line 188 and is collected at decontaminated product collection 182.

In one embodiment using 7,8-dimethyl-10-ribityl isoalloxazine from Sigma Chemical Company as the photosensitizer, a light guide from EFOS Corporation, Williamsville, N.Y. composed of optical fibers is used. The system is capable of delivering a focused light beam with an intensity of 6,200 mW/cm$^2$ in the region of 355–380 nm. It is also possible to use interchangeable filters with the system to achieve outputs of 4,700 mW/cm$^2$ in the spectral region of 400–500 nm. In both cases, the output of light in the region of 320 nm and lower is negligible. Light guides of varying dimensions (3, 5 and 8 mm) are available with this system. The light exits the light guide tip with a 21 degree spread. The 8 mm light guide is appropriate, correctly placed, to adequately illuminate the face of the preferred decontamination cuvette which is a standard cuvette used on Cobe Spectra$^7$ disposables sets from Industrial Plastics, Inc., Forest Grove, Oreg.

The flow rate is variable and is determined by the amount of light energy intended to be delivered to the sample. The flow rate is controlled by means of a peristaltic pump from the Cole-Parmer Instrument Company, Vernon Hills, Ill. Flow rates and type of input stream may be controlled via a computer processor as is known to the art.

Figure 22:
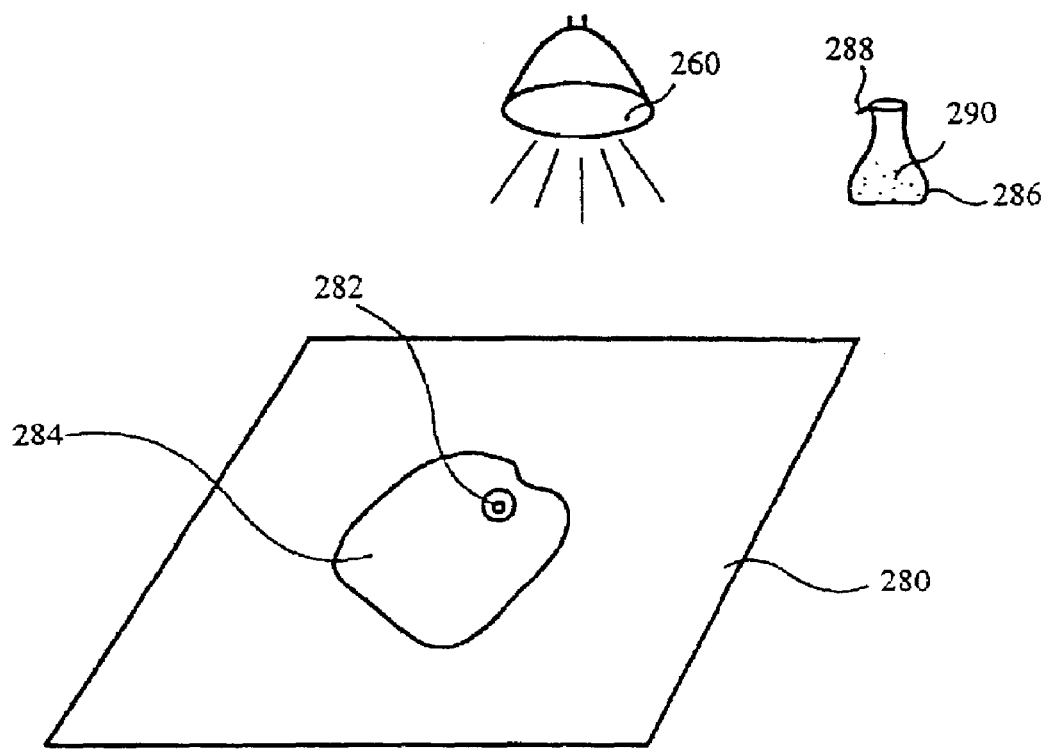
FIG. 22 shows an embodiment of this invention using a bag to contain the fluid being treated and photosensitizer and a shaker table to agitate the fluid while exposing to photoradiation from a light source.

FIG. 22 depicts an embodiment of this invention in which fluid to be decontaminated is placed in a bag 284 equipped with an inlet port 282, through which photosensitizer in powder form 284 is added from flask 286 via pour spout 288. Shaker table 280 is activated to agitate the bag 284 to dissolve photosensitizer 290 while photoradiation source 260 is activated to irradiate the fluid and photosensitizer in bag 284. Alternatively, the bag can be provided prepackaged to contain photosensitizer and the fluid is thereafter added to the bag.

The methods of this invention do not require the use of enhancers such as quenchers or oxygen scavengers, however these may be used to enhance the process by reducing the extent of non-specific cell or protein-damaging chemistry or enhancing the rate of pathogen inactivation. Further preferred methods using non-toxic endogenous photosensitizers and endogenously-based derivative photosensitizers do not require removal of photosensitizers from the fluid after photoradiation. Test results show little or no damage to other blood components, e.g. platelets remain biologically active five days post-treatment.

EXAMPLES

Example 1

Absorbance Profile of 7,8-dimethyl-10-ribityl isoalloxazine

A sample of 7,8-dimethyl-10-ribityl isoalloxazine (98% purity) was obtained from Sigma Chemical Company. A portion of this sample was submitted for analysis using a scanning UV spectrophotometer. The range studied covered the region of 200 to 900 nm. For analysis, the sample was dissolved in distilled water. A sample spectrum from this analysis is shown in FIG. 1.

Results were consistent with those reported in the literature for the absorbance maxima and extinction coefficients for 7,8-dimethyl-10-ribityl isoalloxazine

| Literature λmax (ε) | Measured λmax (ε) |
|---|---|
| 267 (32,359) | 222 (30,965) |
|  | 265 (33,159) |
| 373 (10,471) | 373 (10,568) |
| 447 (12,303) | 445 (12,466) |

Appropriate wavelengths for irradiation are 373 and 445 nm. The extinction coefficients observed at these absorbance maxima is sufficient to ensure adequate activation of the sensitizer in solution.

Example 2

Solubility of 7,8-dimethyl-10-ribityl isoalloxazine

Solubility in Isolyte S, pH 7.4 Media

The maximum solubility of 7,8-dimethyl-10-ribityl isoalloxazine in Isolyte S media was determined as follows:

7,8-dimethyl-10-ribityl isoalloxazine was mixed with Isolyte S until a precipitate was formed. The mixture was agitated at room temperature for one hour and vortex mixed to ensure complete dissolution of the suspended material. Additional 7,8-dimethyl-10-ribityl isoalloxazine was added until a solid suspension remained despite additional vortex mixing. This suspension was then centrifuged to remove undissolved material. The supernatant from this preparation was removed and analyzed using a spectrophotometer. The absorbance values of the solution were determined at 447 nm and 373 nm. From the extinction coefficients that were determined previously, it was possible to estimate the concentration of the saturated solution Concentration (373)=110 μM=42 μg/mL Concentration (447)=109 μM=40.9 μg/mL Solubility in ACD-A Anticoagulant The same procedure described above was repeated using ACD-A Anticoagulant. The values obtained from these measurements were as follows:

Concentration (373)=166 μM=63 μg/mL

Concentration (447)=160 μM=60.3 μg/mL

The values obtained from these studies indicate an upper limit of solubility of the compound that may be expected.

Example 3

Photodecomposition of 7,8-dimethyl-10-ribityl isoalloxazine in Aqueous Media

Figure 3:
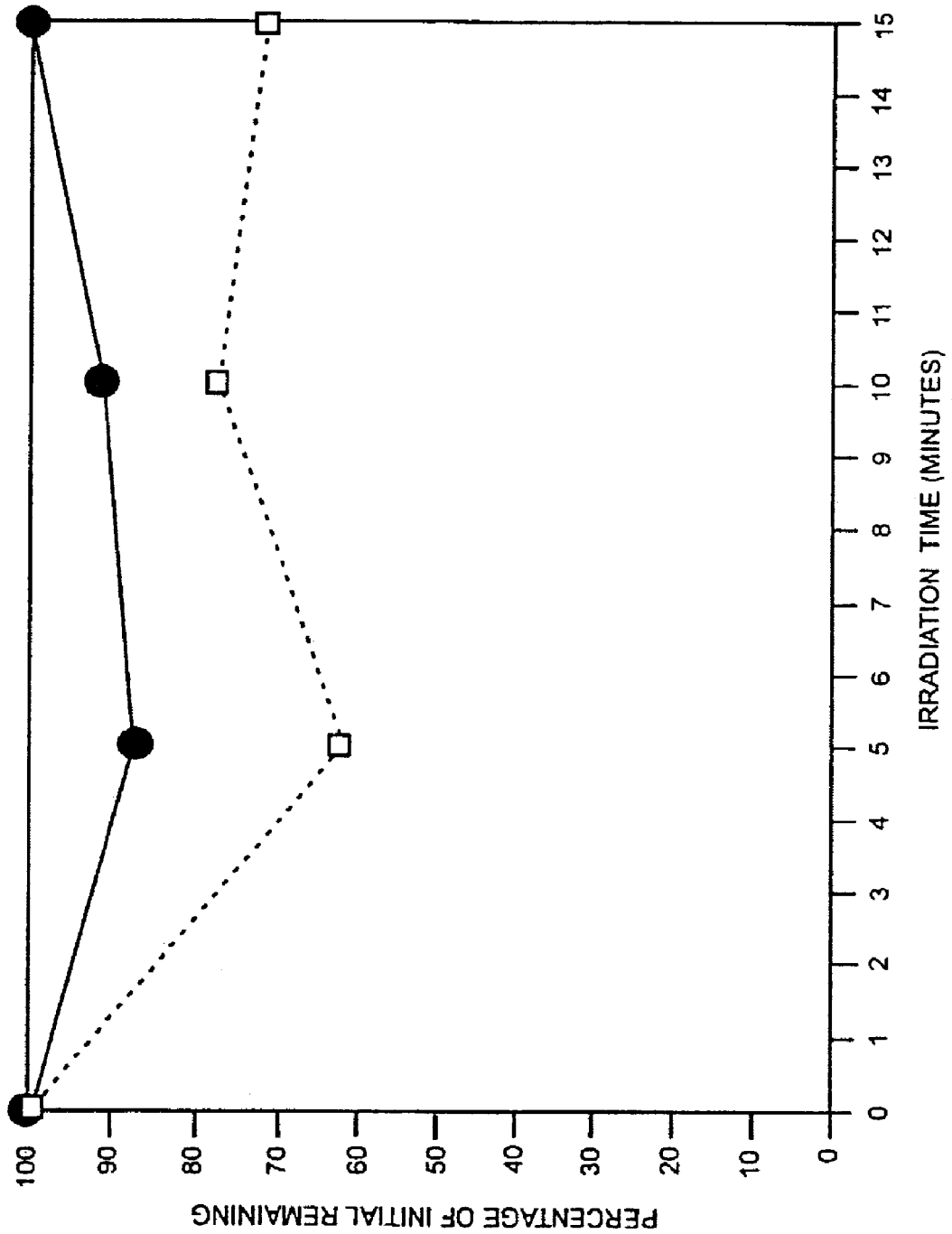
FIG. 3 depicts photodecomposition over time of riboflavin in anticoagulant Acid Citrate Dextrose (ACD) solution. The solid line with circles indicates percent of initial riboflavin remaining at 373 nm. The dotted line with squares indicates percent of initial riboflavin remaining at 447 nm.

A solution of 7,8-dimethyl-10-ribityl isoalloxazine in Sigma ACD-A was prepared at a concentration of 63 μg/mL. This preparation was taken up into a glass pipette and placed in the path of a UV light source (365 nm λmax with filters to remove light below 320 nm). The suspension was irradiated for specific intervals at which aliquots were removed for spectroscopic analysis. The absorbance of the dissolved 7,8-dimethyl-10-ribityl isoalloxazine was monitored at 373 and 447 nm at each time interval. The results are depicted in FIG. 3 and Table 1.

TABLE 1

Photodecomposition of 7,8-dimethyl-10-ribityl isoalloxazine Upon Exposure to UV Light (365 nm) in Acid Solution

| Irradiation Time | % of Initial, 373 nm | % of Initial, 447 nm |
|---|---|---|
| 0 | 100 | 100 |
| 5 | 87.3 | 61.6 |
| 10 | 90.5 | 76.6 |
| 15 | 100 | 70 |

The absorption profile for the solution at 373 nm indicates that no significant decomposition of the reagent occurred over the entire irradiation period. The absorbance of light at this wavelength corresponds to n–π* electronic transitions. The absence of a decrease in the intensity of this peak over time indicates that the ring structure of the molecule is intact despite prolonged irradiation under these conditions. The absorbance of the molecule at 447 nm is due to π–π* electronic state transitions. The decrease in the absorbance of the molecule at this wavelength with increasing irradiation times is indicative of subtle alterations in the resonance structure of the molecule. This change is most likely due to the loss of ribose from the ring structure of the 7,8-dimethyl isoalloxazine backbone and the formation of 7,8-dimethy-lalloxozine as a result. These changes are consistent with literature reports on the behavior of the molecule upon irradiation with UV light.

The apparent lack of decomposition of the ring structure of the molecule is in stark contrast to observations with psoralen-based compounds under similar conditions. During irradiation, a significant fluorescence of the molecule in solution was observed. This behavior of the molecule is consistent with the resonance features of the ring structure and provides a means for the dissipation of energy in the excited state molecule in a non-destructive fashion.

Example 4

Flow System Concept Evaluation

Light Transmission Properties of Existing Spectra Cuvette

The existing Spectra cuvette is composed of polycarbonate. The light transmission properties of this cuvette were measured at 373 and 447 nm by placing the cuvette in the light path of a UV spectrophotometer. The values obtained were as follows:

| Wavelength of Light | % Transmittance |
|---|---|
| 373 nm | 66% |
| 447 nm | 80% |

Figure 4:
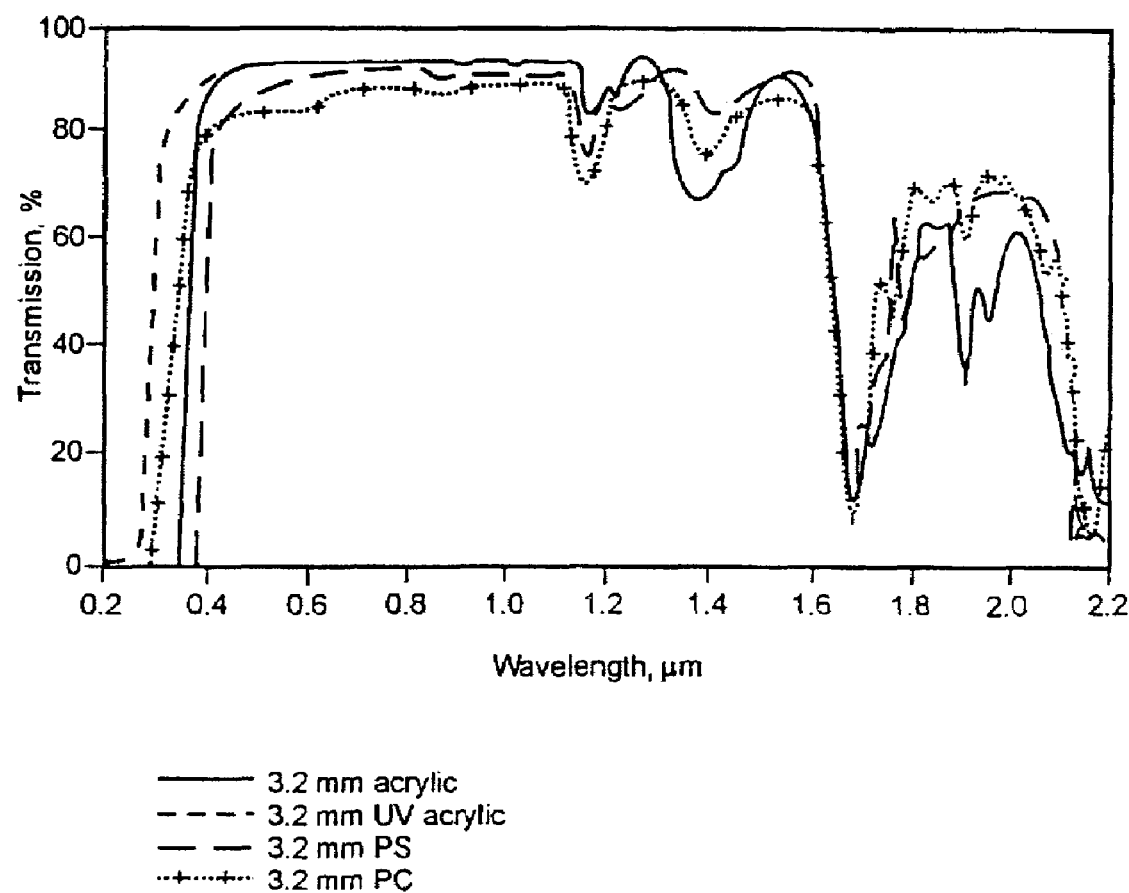
FIG. 4 depicts the transmission profile of various plastic cuvettes as a function of wavelength. The solid line represent a 3.2 mm acrylic cuvette. The dotted line (-----) represents a 3.2 mm UV acrylic cuvette. The dashed line (— ——) represents a 3.2 mm polystyrene (PS) cuvette, and the crossed line indicates a 3.2 mm polycarbonate (PC) cuvette.
Figure 5:
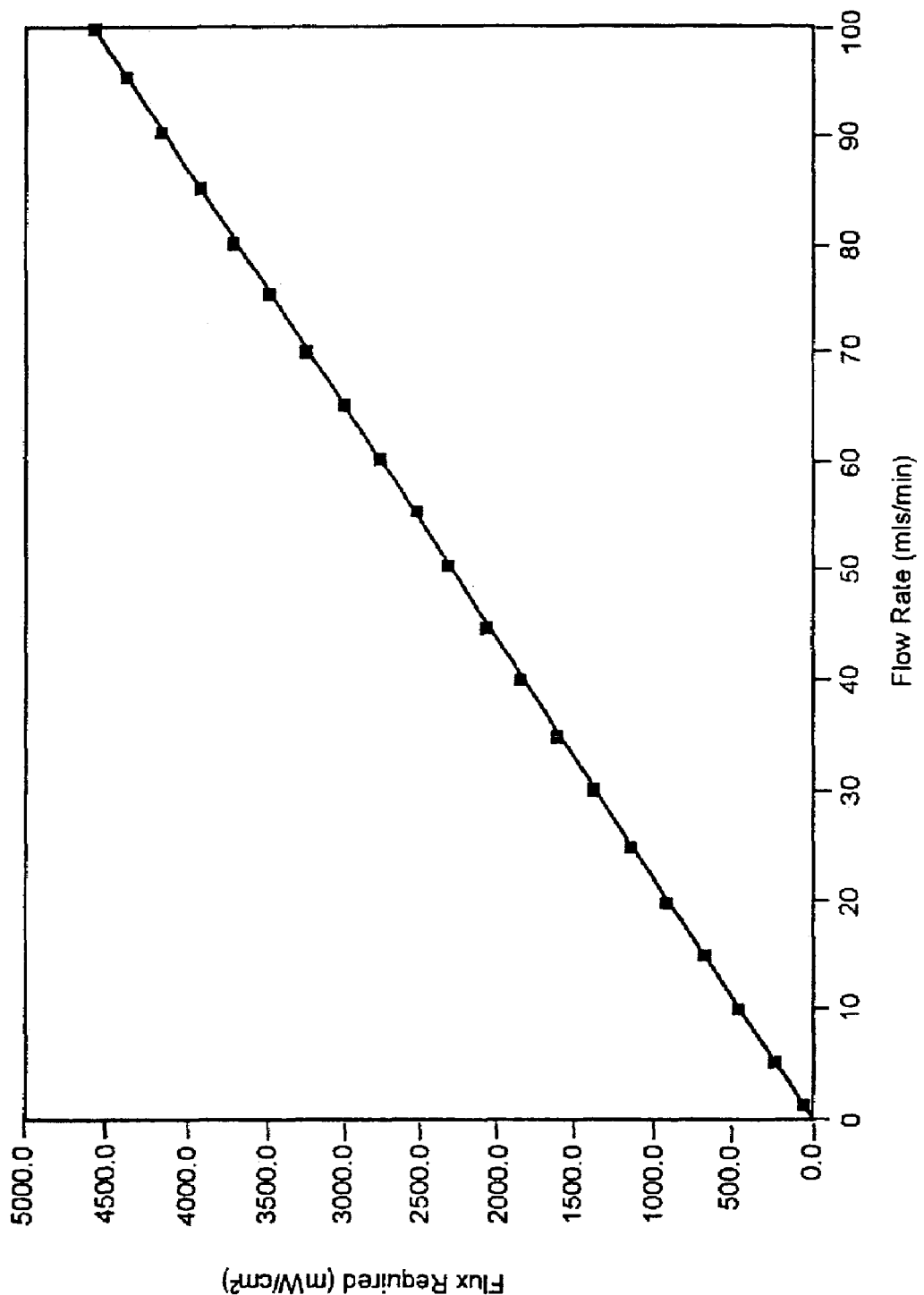
FIG. 5 depicts the light flux required in mW per $cm^2$ as a function of flow rate, i.e. the flux required to deliver one joule/$cm^2$ to a sample in the cuvette.

These results are consistent with those reported in the literature for polycarbonate plastics (see FIG. 4). The literature values indicate a steep shoulder for the transmission of light through polycarbonates in the region of 300 nm. For the region above 350 nm, the light transmission properties are adequate for this application.

Light Flux Requirements Calculated as a Function of Flow Rates

In order for a flow system to be feasible, the sample must be provided with an adequate flux of light during its presence in the beam path. If the proposed Spectra cuvette were to serve this purpose, then it is possible to estimate the light flux requirements as a function of flow rates through the cuvette as follows:

The volume of solution present in the irradiation zone of the cuvette is ca. 0.375 mls. The transit time for a cell in this region of the cuvette can be determined from the following equation:

$$T = \frac{\text{Volume of Cuvette (mls)}}{\text{Flow Rate (mls/min)}}$$

At 100 mls per minute, the transit time (T) would be 0.00375 min=0.225 seconds.

The energy to which a sample is exposed is dependent on the flux according to the following equation:

$$\text{Energy (E, Joules/cm}^2) = \frac{\text{Flux }(\phi, \text{mW/cm}^2) * \text{Time (T, sec.)}}{1000}$$

If we assume that 1 Joule/cm² is required to activate the sensitizer adequately and the transit time (T) is 0.22 seconds (i.e., flow rate of 100 mls/min through the cuvette), then the required Flux during the sample=s transit through the cuvette is 4,545 mW/cm². A graph depicting the relationship of the required flux from the light source to flow rates through the cuvette is provided in FIG. 5.

These results indicate that, for a flow system to, operate properly, UV sources with outputs in the region of Watts/cm² are required.

Figure 2:
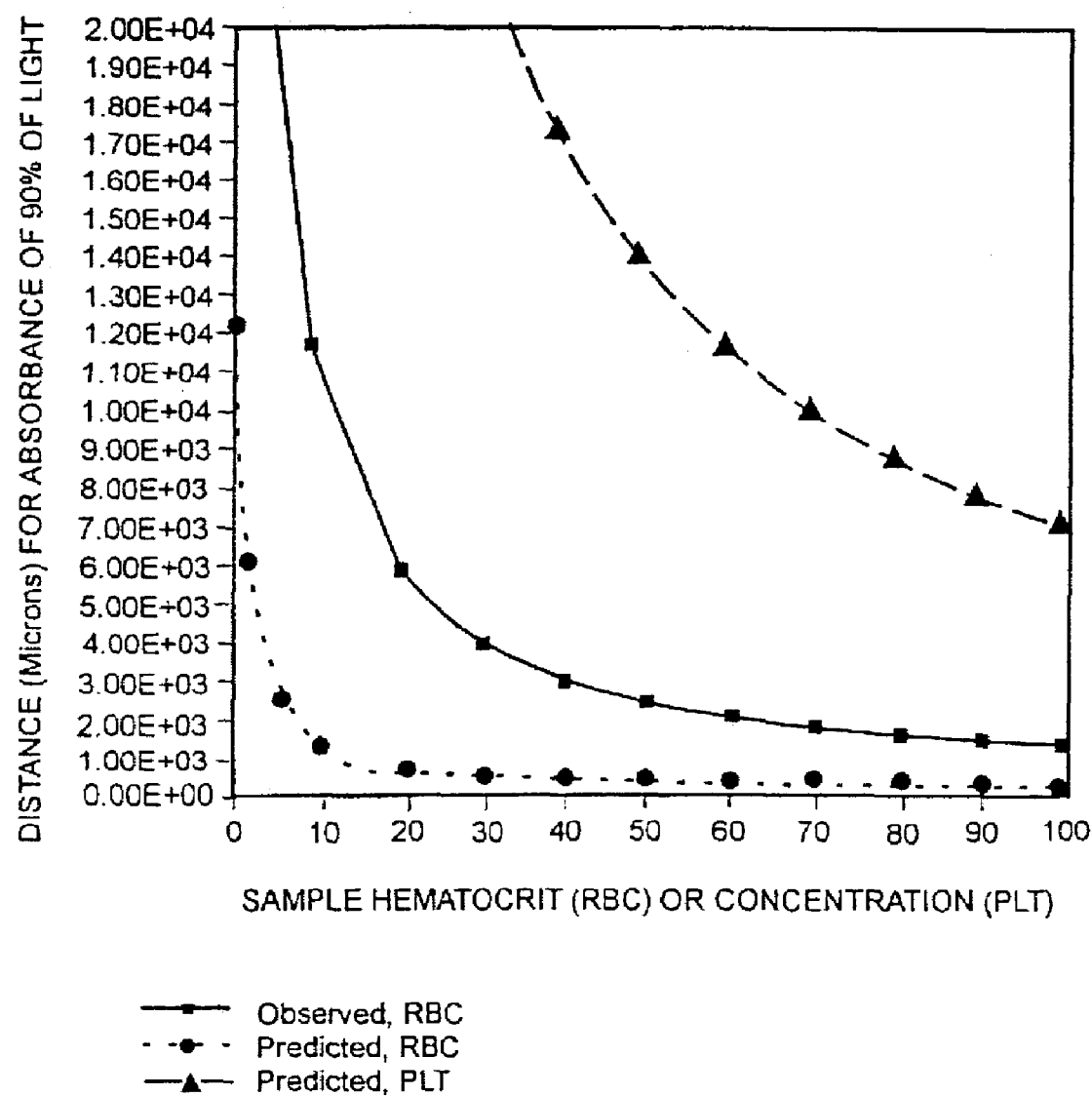
FIG. 2 depicts a correlation of light absorbance and hematocrit observed and predicted for red blood cells, and predicted for platelets.

FIG. 2 shows how absorbance should vary with concentration of platelets.

Example 6

Effects of Virus Inactivation Treatment on Platelet In Vitro Parameters

Effects of virus inactivation treatment on platelet in vitro parameters were evaluated. Platelet preparations were treated with 7,8-dimethyl-10-ribityl isoalloxazine in combination with UV light. Various in vitro parameters were used as monitors of platelet function in order to determine the extent of changes induced by the treatment conditions. Factors such as energy level of UV light exposure, dose of 7,8-dimethyl-10-ribityl isoalloxazine used, and sample processing conditions were examined for their impact on platelet quality post-treatment. Results from this study are used to establish an appropriate treatment window for inactivation of HIV-1 without compromising platelet function.

Samples were prepared with three different concentrations of 7,8-dimethyl-10-ribityl isoalloxazine. Platelets obtained from a standard Spectra LRS collection were used for these studies.

Starting samples were centrifuged to concentrate the platelet pellet. The pellet was resuspended in a 70:30 (Isolyte S, pH 7.4; McGaw, Inc. Media:Plasma) solution. 7,8-dimethyl-10-ribityl isoalloxazine at the specified concentration, was present in the plasma:media mixture. The platelet suspension was then passed through a UV irradiation chamber at one of three specified flow rates. The flow rates were directly correlated to the energy level of exposure for the cells/media mixture which passes through the irradiation chamber. After flowing through the irradiation chamber, samples were stored in a citrate plasticized sampler bag for subsequent analysis.

Following irradiation, in vitro measurements of platelet function, including hypotonic shock response (HSR), GMP-140 expression, pH, $pCO_2$, $pO_2$, platelet swirl, and cell count, were evaluated in order to determine the effects of the treatment protocol on cell quality.

Platelet quality was monitored as a function of irradiation conditions (sensitizer concentration and flow rates/Energy levels). The platelet quality includes parameters such as HSR response, GMP-140 activation, etc. The flow rates that are studied can be related to the Energy of exposure as follows:

$$\text{Transit Time(T, sec)} = \text{Exposure Time} = \frac{0.375 \text{mls}}{(F_r/60)}$$

$F_r$ = Flow Rate(mls/min)

0.375mls = Cuvette Volume(mls)

$T(\text{sec}) = 22_{F_r}$ $$\text{Energy (Joules/cm}^2) = \frac{\text{Flux }(\phi, \text{mW/cm}^2) * T(\text{sec})}{1000}$$

$$E = \frac{\phi * 0.022}{F_r}$$

The effect of energy of UV exposure and concentration of 7,8-dimethyl-10-ribityl isoalloxazine on the stability and viability of treated platelets was evaluated. Three energy levels and three concentration levels were evaluated as follows:

| | |
|---|---|
| Energy Levels: | 1, 5, 9 J/cm²* |
| 7,8-dimethyl-10-ribityl isoalloxazine Concentrations: | 1, 50, 100 μM** |

*Levels of total energy exposure were determined by the flow rate of the suspension through the irradiation chamber in accordance with the conversion chart of Table 4.
**Since the media is diluted 70:30 (Media:Plasma) the stock concentration of 7,8-dimethyl-10-ribityl isoalloxazine in media alone prior to mixing with the plasma was adjusted appropriately. This required starting concentrations in Isolyte S of 1.43, 71.4, and 143 μM.

TABLE 4

Energy Exposure Levels as a Function of Flow Rate Through the Irradiation Chamber

| Energy Delivered (J/cm²) | Flow Rate (mls/min) | Time to process 20 mls (minutes) |
|---|---|---|
| 1 | 16.90 | 1.18 |
| 2 | 8.45 | 2.37 |
| 3 | 5.83 | 3.55 |
| 4 | 4.22 | 4.73 |
| 5 | 3.38 | 5.92 |
| 6 | 2.82 | 7.10 |
| 7 | 2.41 | 8.29 |
| 8 | 2.11 | 9.47 |
| 9 | 1.88 | 10.65 |
| 10 | 1.69 | 11.84 |

Flux=3640 mW/cm²; chamber volume=0.117 mls.

Values for treated samples were compared to control groups. The control samples included the following:

Untreated Sample in Plasma (Historical Control)
+Flow-UV-7,8-dimethyl-10-ribityl isoalloxazine Procedure A normal donor platelet apheresis product was obtained from an AABB accredited blood banking facility. The sample was collected using standard Spectra LRS procedures. All manipulations or procedures described below were performed with standard laboratory safety procedures and methods. The unit number and blood type were recorded. All samples were used within 24 hours of collection. Aseptic procedure was followed for all sample transfers and processing steps.

The sample was transferred to a 500 mls PVC transfer pack and centrifuged at 5000×g for five minutes to pack the platelets. Plasma was then removed from the platelet pellet using a standard plasma press. The plasma was retained for further use. The plasma removed from the cell pellet was then mixed with a stock solution of Isolyte S, pH 7.4; McGaw, Inc. This stock solution of media was prepared by adding a pre-determined amount of 7,8-dimethyl-10-ribityl isoalloxazine to Isolyte S to provide final concentrations of 1.43, 71.4, and 143 µM. Following addition of 7,8-dimethyl-10-ribityl isoalloxazine the stock solution was filtered through a 0.22 µM sterile filter. The stock solution was then mixed with autologous plasma in a 70:30 (v:v) ratio to provide final 7,8-dimethyl-10-ribityl isoalloxazine concentrations of 1, 50, and 100 µM respectively. During preparation of the 7,8-dimethyl-10-ribityl isoalloxazine stock solutions, care was taken to avoid exposure to light. Samples were prepared according as follows:

| | |
|---|---|
| 1 µM | 2 samples |
| 100 µM | 2 samples |
| 50 µM | 1 sample |

The platelet pellet was then resuspended in the plasma:media mixture to the original volume of the starting sample. The sample was connected to a flow apparatus comprising a container for cells and photosensitizer, a container for media, said containers being connected via valved lines to a single line for mixed cells/sensitizer and media equipped with a pump. Mixed cells/sensitizer and media were flowed into a cuvette held in a holder with a mirrored wall, irradiated by a light source. This irradiation chamber was equipped with a temperature probe. After passing through the cuvette, fluid was collected in a product bag.

The tubing set was initially primed with Isolyte S media. Five minutes prior to the start of the test sample flow, the light source was activated. Temperature was monitored during this interval and kept lower than 32° C. in the irradiation chamber.

The flow rate for the sample through the irradiation chamber was determined by the chart of Table 4. Flow rates which provide total irradiation energy levels of 1, 5 and 9 J/cm$^2$ were utilized according to the following testing matrix:

Sample Run #1: 7,8-dimethyl-10-ribityl isoalloxazine Concentration=1 µM
   A. +7,8-dimethyl-10-ribityl isoalloxazine+1 J/cm$^2$
   B. +7,8-dimethyl-10-ribityl isoalloxazine+9 J/cm$^2$ Sample Run #2: 7,8-dimethyl-10-ribityl isoalloxazine=100 µM
   A. +7,8-dimethyl-10-ribityl isoalloxazine+1 J/cm$^2$
   B. +7,8-dimethyl-10-ribityl isoalloxazine+9 J/cm$^2$ Sample Run #3: 7,8-dimethyl-10-ribityl isoalloxazine=50 µM
   A. +7,8-dimethyl-10-ribityl isoalloxazine+5 J/cm$^2$ Sample Run #4: Control Sample, 7,8-dimethyl-10-ribityl isoalloxazine=0 µM
   A. +Flow-UV-7,8-dimethyl-10-ribityl isoalloxazine All samples were identified by the run number and sample letter designation corresponding to treatment condition (i.e., 1A). Each sample set was run for a total of 2 replicates. The order in which samples were treated was determined by assignment according to a random number generator.

A sample volume of 20 mls per run condition was collected for each sample. These samples were collected into citrate plasticized sampling bags (53 mls total volume) and stored for analysis. The temperature of the sample and the irradiation chamber was noted at the start, mid-point, and end of each run.

An initial aliquot from each preparation was removed post-treatment for analysis. Parameters for analysis included cell count, pH, pCO2, pO2, platelet swirl, HSR, and GMP-140 analysis. The remaining portion of the sample was placed in an end-over-end platelet agitator in a +22 incubator and stored for five days post-treatment. On day 5, a second aliquot was removed and analyzed for the same in vitro parameters.

The following equipment was used: Nikon Labophot microscope; Serono-Baker System 9000 Hematology Analyzer; analytical balance; platelet incubator (+22 Celsius) and rotator; laboratory refrigerator (+4 Celsius); Mistral 3000i Centrifuge; Corning Blood Gas Analyzer; Becton-Dickinson FACSCALIBUR Flow Cytometer; UV irradiation chamber; UV radiometer (UVX Radiometer, UVP, Inc.); EFOS Ultracure 100SS Plus (365 nm maximum output and 340 nm bandpass filters); and temperature probe (thermocouple).

Results for each set of test variables were compared for the defined conditions of energy of exposure and concentration of 7,8-dimethyl-10-ribityl isoalloxazine. Direct comparison to the untreated control sample was made and significant differences defined by a probability p>0.05 from a paired, one-tailed, Student's T-Test analysis.

01 The results from these studies were summarized as follows:
   At sensitizer concentrations in excess of 10 µM and platelet concentrations above 1.5E+06/µL, there was a drop in sample pH by day 2. The pH declined steadily beyond day 2 of storage reaching unacceptable levels (<6.5) by day 3 of storage. All other in vitro parameters followed the pattern observed with sample pH.

02 This decrease in sample pH occurred regardless of whether or not the sample was exposed to UV light.

03 At platelet concentrations of 5.4E+05/µL, there was no drop in sample pH after extended storage at any sensitizer concentration studied up to 100 µM.

At sensitizer concentrations up to 10 μM, platelet concentrations above 1.5E+06/μL, and UVA levels up to 10 J/cm2, measured platelet properties were comparable to control, untreated cells. These remained comparable to control levels after five or more days of storage post-treatment.

These studies on platelet function post-treatment provided a clear window in which cell properties were maintained at levels comparable to untreated cells. The results also indicated that by varying the storage or treatment conditions for the cells this window can be expanded. The observed effect of 7,8-dimethyl-10-ribityl isoalloxazine with or without UV light on sample pH suggests a metabolic effect of this additive which may be moderated by changes in the storage or processing conditions of the samples.

Example 7

Measurements of Shear Stresses on Red Cells as a Function of Flow Rate and Sample Hematocrit The low levels of UV light penetration into red cell samples at high hematocrits raised the need to understand the effects of passing red cells through narrow openings in the light path. Reduction in sample thickness in the light path should increase delivery of UV dose at high sample hematocrits. In order to confirm this approach, several pressure drop measurements were undertaken using openings of varying dimensions. A pressure gauge was placed in line with a peristaltic pump both upstream and downstream from the narrowed openings. Whole blood of varying hematocrits was passed through the openings at controlled flow rates. Differences in the pressure readings at both locations permitted direct measurement of the pressure drop across the opening. Using this value and the dimensions of the opening, it was possible to determine the shear stress experienced by the red cells as they passed through the narrowed cell using the following equation:

$$\Delta P = \frac{8\mu LQ}{gd^3 w} \quad \text{Pressure Drop}$$

$$T_w = \frac{4\mu Q}{gwd^2} \quad \text{Shear Stress}$$

For blood,
μ=Viscosity=0.0125/(1−Hematocrit)
g=gravitational constant=981
Q=Flow Rate=mls/sec
l, w, d=Dimensions of opening in cm

TABLE 5

Measurement of Shear Stress on Red Cells As Functions of Flow Rate and Sample Hematocrit

| | | 0.08 × 0.008 | Dpmeas (dynes/cm²) | 0.08 × 0010 | Dpmeas (dynes/cm²) | 0.08 × 0.012 | Dpmeas (dynes/cm²) |
|---|---|---|---|---|---|---|---|
| 41% HCT | Q = 3.38 | 1.5 | 95.9 | 1.0 | 77.6 | 0.0 | 0.0 |
| 64% HCT | Q = 3.38 | 4.0 | 255.8 | 3.0 | 232.9 | 2.0 | 182.1 |
| 41% HCT | Q = 16.9 | 9.7 | 618.4 | 7.0 | 543.4 | 4.7 | 425.3 |
| 61% HCT | Q = 16.9 | 20.7 | 1321.9 | 12.3 | 957.2 | 8.7 | 789.6 |
| | | 0.10 × 0.008 | Dpmeas (dynes/cm²) | 0.1 × 0.010 | Dpmeas (dynes/cm²) | 0.1 × 0.012 | Dpmeas (dynes/cm²) |
| 41% HCT | Q = 3.38 | 2.0 | 93.7 | 1.0 | 60.3 | 1.0 | 73.5 |
| 64% HCT | Q = 3.38 | 4.5 | 210.8 | 3.0 | 180.9 | 2.0 | 146.9 |
| 41% HCT | Q = 16.9 | 12.7 | 593.6 | 7.0 | 422.1 | 4.7 | 343.0 |
| 61% HCT | Q = 16.9 | 23.3 | 1093.0 | 14.7 | 884.6 | 12.0 | 881.4 |
| | | 0.15 × 0.008 | Dpmeas (dynes/cm²) | 0.15 × 0.010 | Dpmeas (dynes/cm²) | 0.15 × 0.012 | Dpmeas (dynes/cm²) |
| 41% HCT | Q = 3.38 | 3.0 | 97.4 | 1.2 | 49.2 | 1.0 | 49.0 |
| 64% HCT | Q = 3.38 | 6.5 | 211.0 | 3.5 | 143.5 | 2.0 | 97.9 |
| 41% HCT | Q = 16.9 | 15.3 | 497.7 | 8.3 | 341.6 | 5.7 | 277.6 |
| 61% HCT | Q = 16.9 | 35.7 | 1158.1 | 18.0 | 738.1 | 12.7 | 620.4 |

In previous experiments, it was determined that shear stresses of 1,000–2,000 dynes/cm² for intervals of 1–10 minutes or levels of 5,000–7,000 dynes/cm² for intervals of approximately 10 msec were sufficient to induce red cell hemolysis. Only in the case of the highest sample hematocrit (61%) and highest flow rate (16.9) did values exceed 1,000 dynes/cm². This occurred only for openings of the narrowest width (0.008 inches).

Values for the light penetration depth using the proposed configuration indicate that delivery in sufficient UV energy to drive virus inactivation processes is achievable even for samples with high hematocrits.

Results from shear stress analysis on red cell samples subjected to flow indicate that flow path dimensions may be significantly reduced and high flow rates maintained without risking red cell hemolysis.

Example 8

A platelet concentrate was mixed with the platelet additive solution Isolyte S at a ratio of 20:80 platelet concentrate:Isolyte S. Mixtures of platelet concentrates and platelet additive solutions are referred to herein as in "media." Platelet concentrate without additive solution is referred to herein as in "plasma." Both were spiked with *Listeria monocytogenes*. Vitamin K5 was then added to each in the amount of 300 μg/mL B. Each was then exposed to UV, visible or room light in the cuvette apparatus of FIG. 6 with the results shown in Table 6.

TABLE 6

| | Log Inactivation (cfu/mL) | |
|---|---|---|
| | K5 in Media | K5 in Plasma |
| UV, 40 J/cm² | 4.2 Logs | 0.1 Logs |
| VIS, 40 J/cm² | 4.2 Logs | 0.1 Logs |
| Room Light | 0 Logs | 0 Logs |

UV Light = 365 nm
VIS Light = 419 nm
Pathogen = *Listeria monocytogenes*
Concentration of K5 = 300 μg/mL Example 9

Media and plasma as described above containing vitamin K5 were spiked with bacteria and irradiated or exposed to room light only (K5-light) as shown in Table 7, and growth evaluated after three days of incubation. Inactivation of some species was seen in the absence of irradiation.

TABLE 7

| | | Media | | Plasma | |
|---|---|---|---|---|---|
| | Spike Level | | | K5 – | |
| | (cfu/mL) | K5 – Light | K5 + Light | Light | |
| *P. aeruginosa* | 3.4 Logs | – | – | – | |
| *S. aureus* | 2.1 Logs | – | – | + | + |
| *S. epidermidis* | 3.2 Logs | – | + | – | – |
| *L. monocytogenes* | 3.5 Logs | – | – | + | + |
| *E. coli* | 3.1 Logs | – | – | + | – |

UV Light = 365 nm, 40 J/cm²
+ = Growth detected after three days incubation
– = No Growth detected after three days incubation
Concentration of K5 = 300 μg/mL Example 10

Media made using a platelet concentrate as described in Example 8 and Isolyte S at a ratio of Isolyte S:platelet concentrate of 70:30 and containing 300 μg/mL vitamin K5 was spiked with several species of bacteria and irradiated at energy levels of 30 and 60 J/cm². Inactivation as a function of energy of irradiation is set forth in Table 8 and FIG. 7.

TABLE 8

| Energy (J/cm²) | *S. aureus* | *S. epidermidis* | *L. monocytogenes* | *E. coli* |
|---|---|---|---|---|
| 0 | 4.3 | 2.6 | 2.8 | 3.5 |
| 30 | 3.6 | 2.7 | 2 | 2 |
| 60 | 3.2 | 2.5 | 1 | 1 |

Example 11

Figure 8:
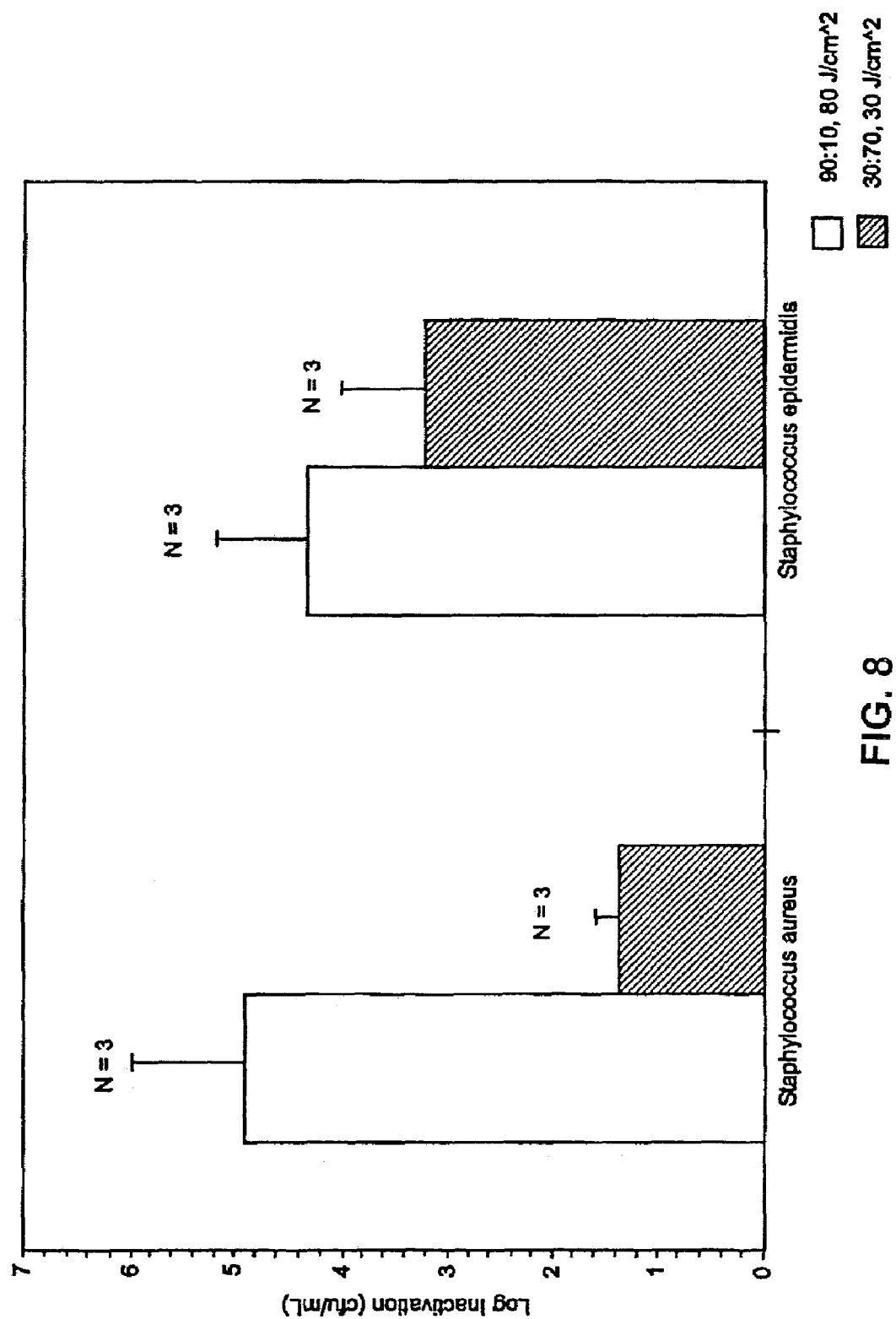
FIG. 8 depicts inactivation of bacteria as a function of platelet preparation and energy of irradiation, using 90% platelets and 10% platelet additive solution (90:10) and 30% platelets with 70% additive solution (30:70).

To platelet concentrate as described in Example 8 and to 70:30 media as described in Example 10 was added 10 μM of 7,8-dimethyl-10-ribityl isoalloxazine. The platelet concentrate and media were spiked with *S. aureus* or *S. epidermidis*, and irradiated at 80 J/cm² and 30 J/cm² and inactivation measured as above. Results are shown in FIG. 8.

Example 12

To plasma concentrate as described in Example 8 contained in a standard blood bag was added 25 μM 7,8-dimethyl-10-ribityl isoalloxazine in powder form. The bag was spiked with bacteria as shown in Table 9, agitated and exposed to 120 J/cm² radiation. Inactivation results are set forth in Table 9.

TABLE 9

| Pathogen | Log Inactivation (cfu/mL) |
|---|---|
| *S. aureus* | 1.7 Logs |
| *S. epidermidis* | 3.5 Logs |
| *P. aeruginosa* | 3.6 Logs |
| *E. coli* | 4.1 Logs |

Example 13

To platelet concentrate as described in Example 8 was added 7,8-dimethyl-10-ribityl isoalloxazine, alloxazine mononucleotide, or 7-8-dimethyl alloxazine, followed by spiking with *S. aureus* or *S. epidermidis*, and irradiation at 80 J/cm². Inactivation results are shown in Table 10.

TABLE 10

| | Log Inactivation (cfu/mL) | |
|---|---|---|
| | *Staphylococcus aureus* | *Staphylococcus epidermidis* |
| 7,8-dimethyl-10-ribityl isoalloxazine, 10 μM | 1.9 Logs | 4.1 Logs |
| alloxazine mononucleotide, 10 μM | 1.6 Logs | 5.6 Logs |
| 7-8-dimethyl alloxazine, 7 μM | 1.6 Logs | 2.9 Logs |

Example 14

Figure 9:
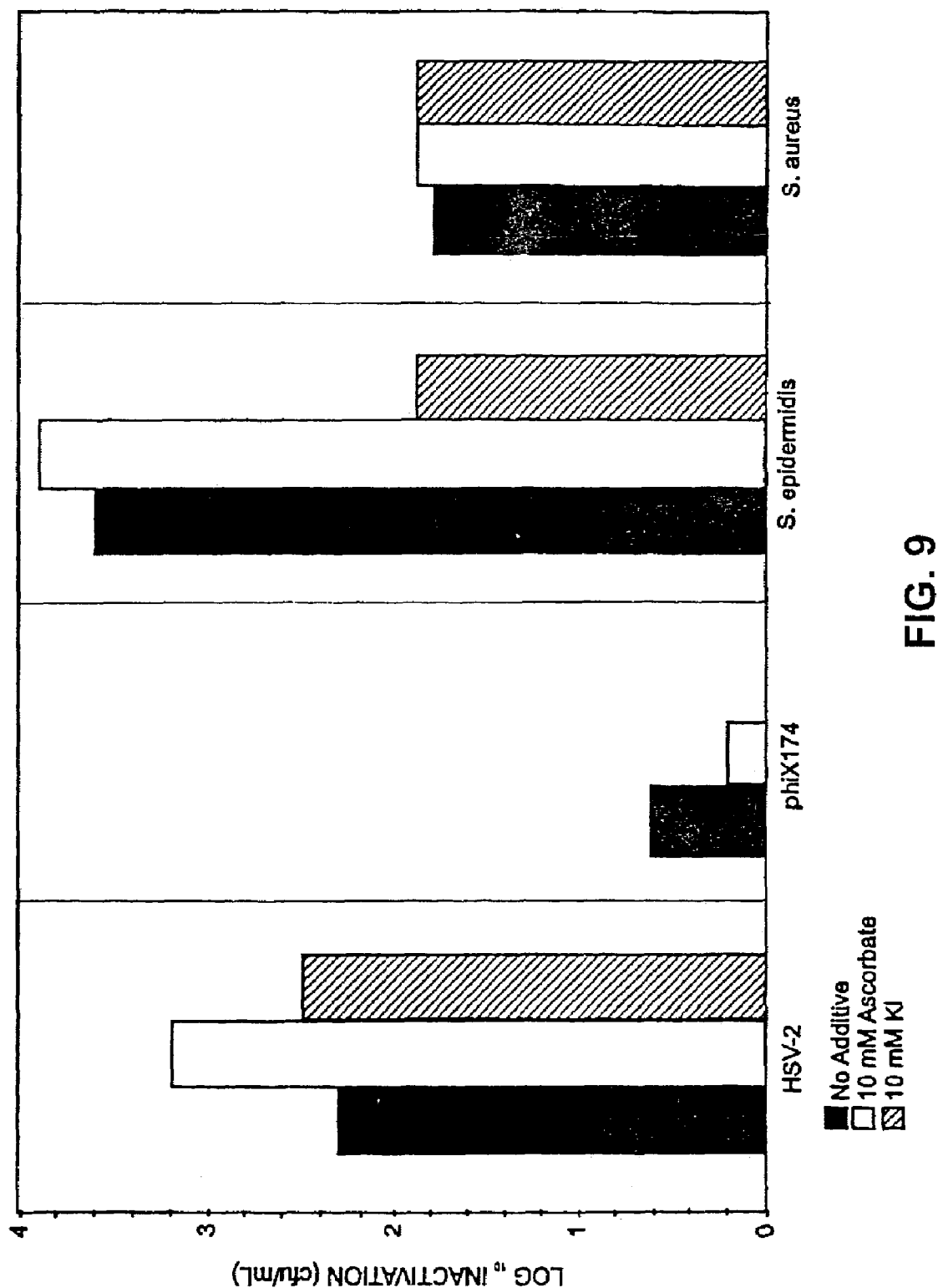
FIG. 9 shows the effect on inactivation of virus, bacteriophage and bacteria of adding antioxidants to platelet concentrate.

To platelet concentrate of Example 8 was added 10 µM 7,8-dimethyl-10-ribityl-isoalloxazine. Aliquots contained no additive, 10 mM ascorbate or 10 mM KI as a Aquencher@ or antioxidant. The solutions were spiked with HSV-2, ΦX174, *S. epidermidis* or *S. aureus* and irradiated at 80 J/cm$^2$. Results are shown in FIG. 9.

Example 15

Figure 10:
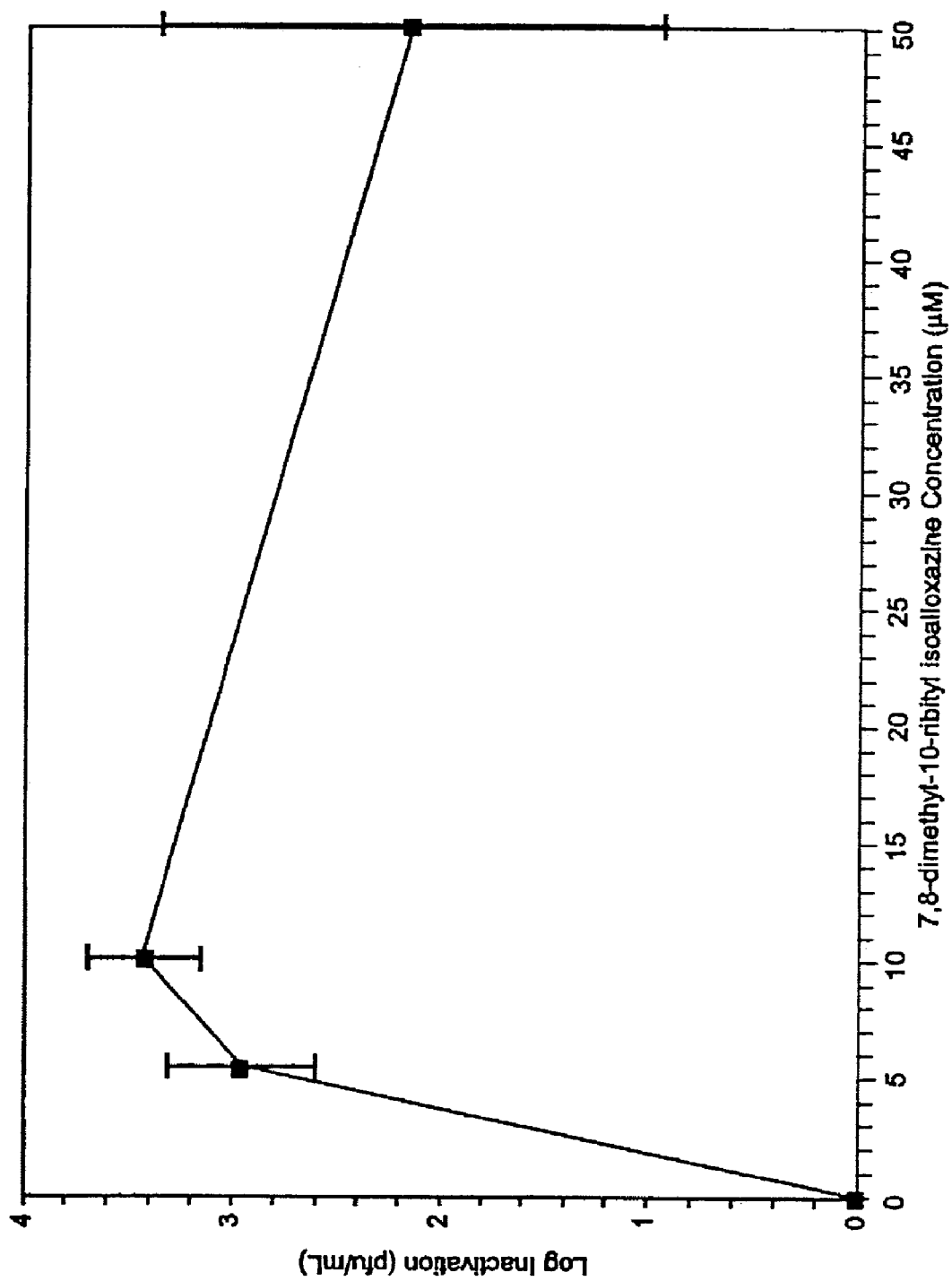
FIG. 10 shows the inactivation curve for Herpes Simplex type II virus as a function of concentration of photosensitizer at an energy of irradiation of 20 J/$cm^2$ using half ultraviolet and half visible light.

To platelet concentrates of Example 8 were added varying concentrations of 7,8-dimethyl-10-ribityl-isoalloxazine. These solutions were spiked with herpes simplex virus type II (HSV-II), a double-stranded DNA envelope virus. Irradiation was done at 80 J/cm$^2$. The experiment was replicated three times. In all three trials complete inactivation was achieved. Results are shown in FIG. 10.

Example 16

Figure 11:
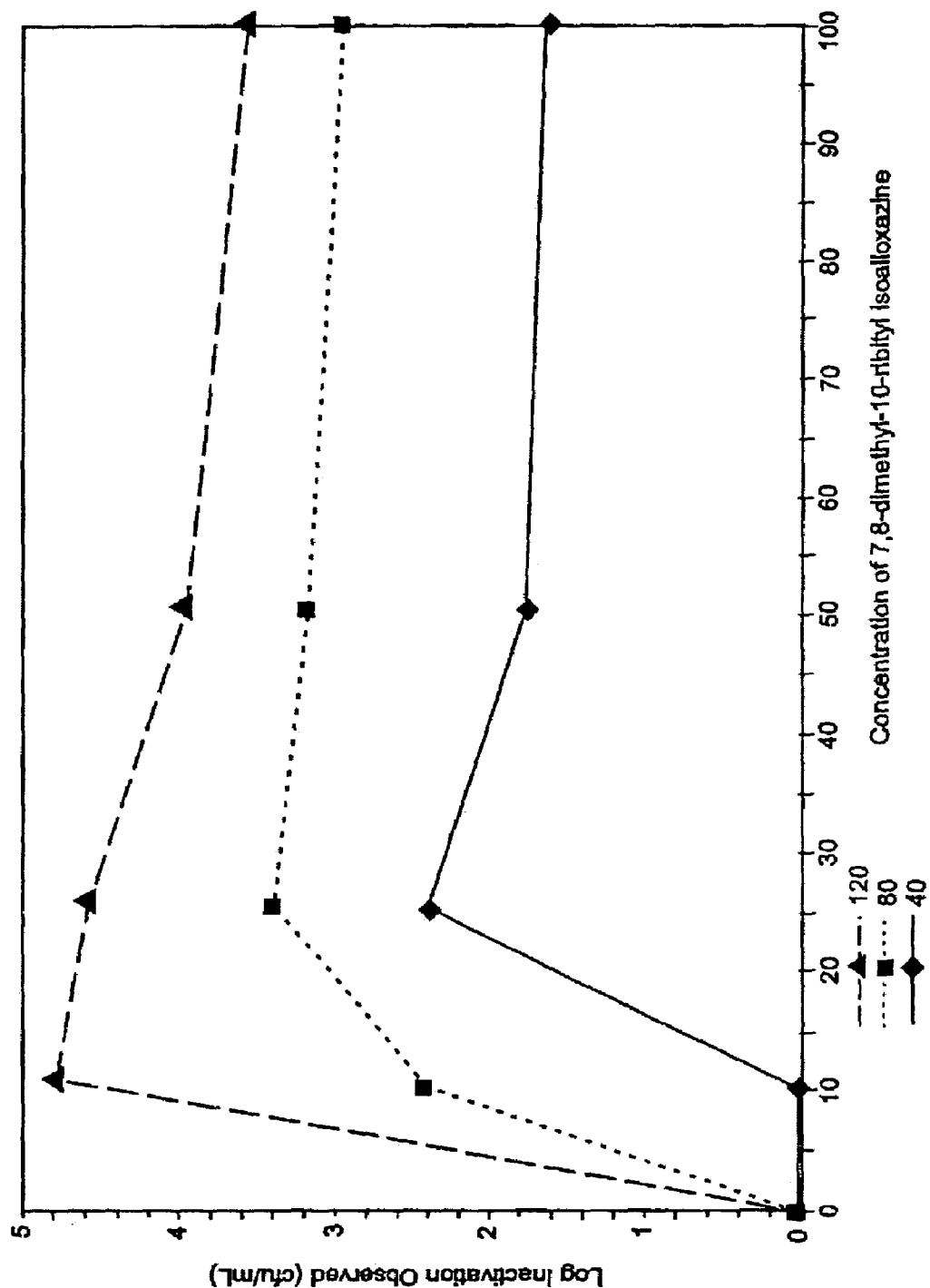
FIG. 11 shows inactivation of *S. epidermidis* at varying concentrations of photosensitizer and energies of irradiation.

The protocol of Example 15 was followed using *S. epidermidis* instead of HSV II at energies of irradiation of 40, 80 and 120 J/cm$^2$. Inactivation results are shown in FIG. 11.

Example 17

Figure 12:
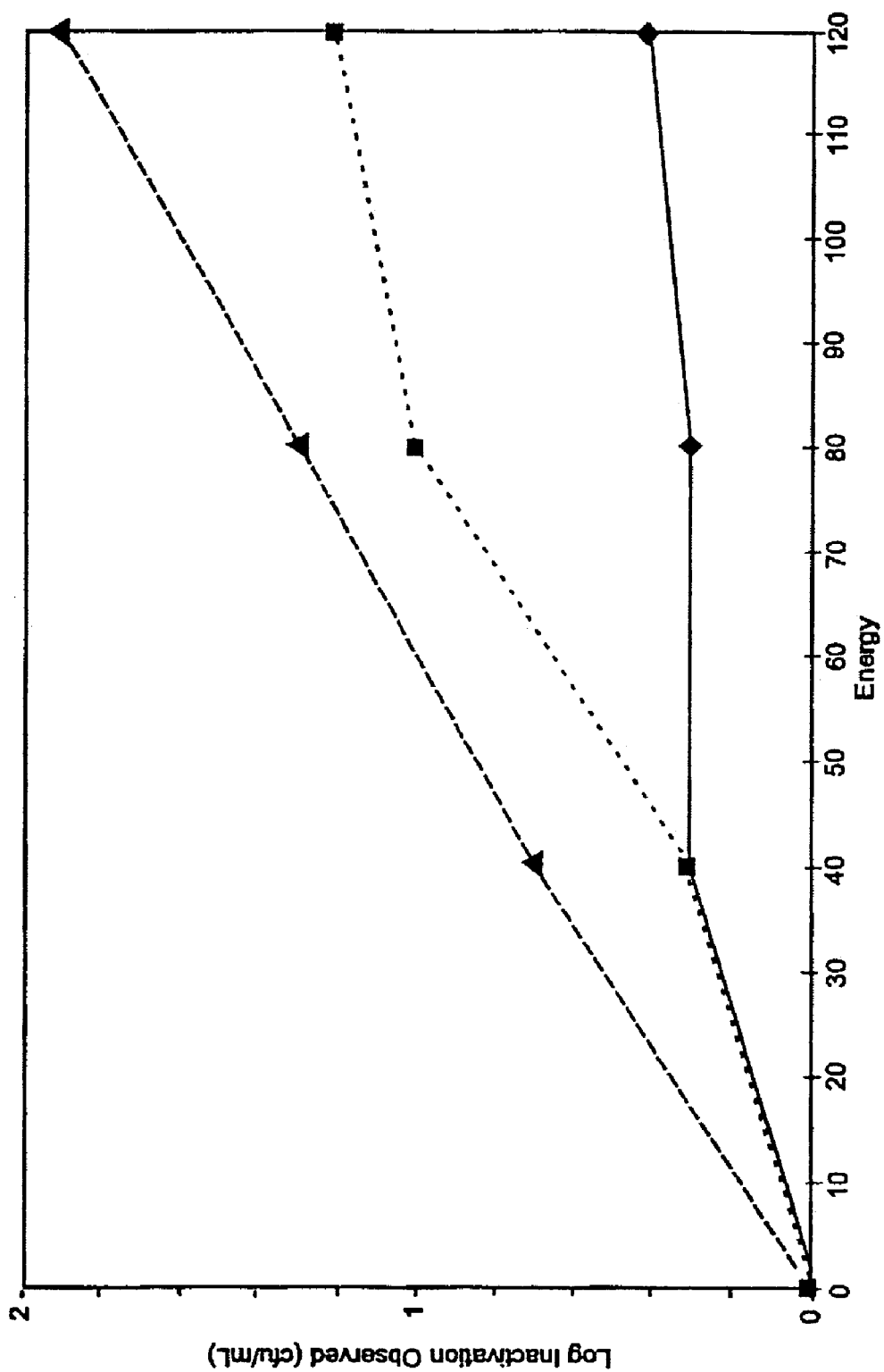
FIG. 12 shows inactivation of ΦX174 at varying concentrations of photosensitizer and energies of irradiation.

The protocol of Example 15 was followed using ΦX174, a single stranded DNA bacteriophage, at varying concentrations of 7,8-dimethyl-10-ribityl-isoalloxazine and energies of irradiation. Inactivation results are shown in FIG. 12.

Example 18

Figure 13:
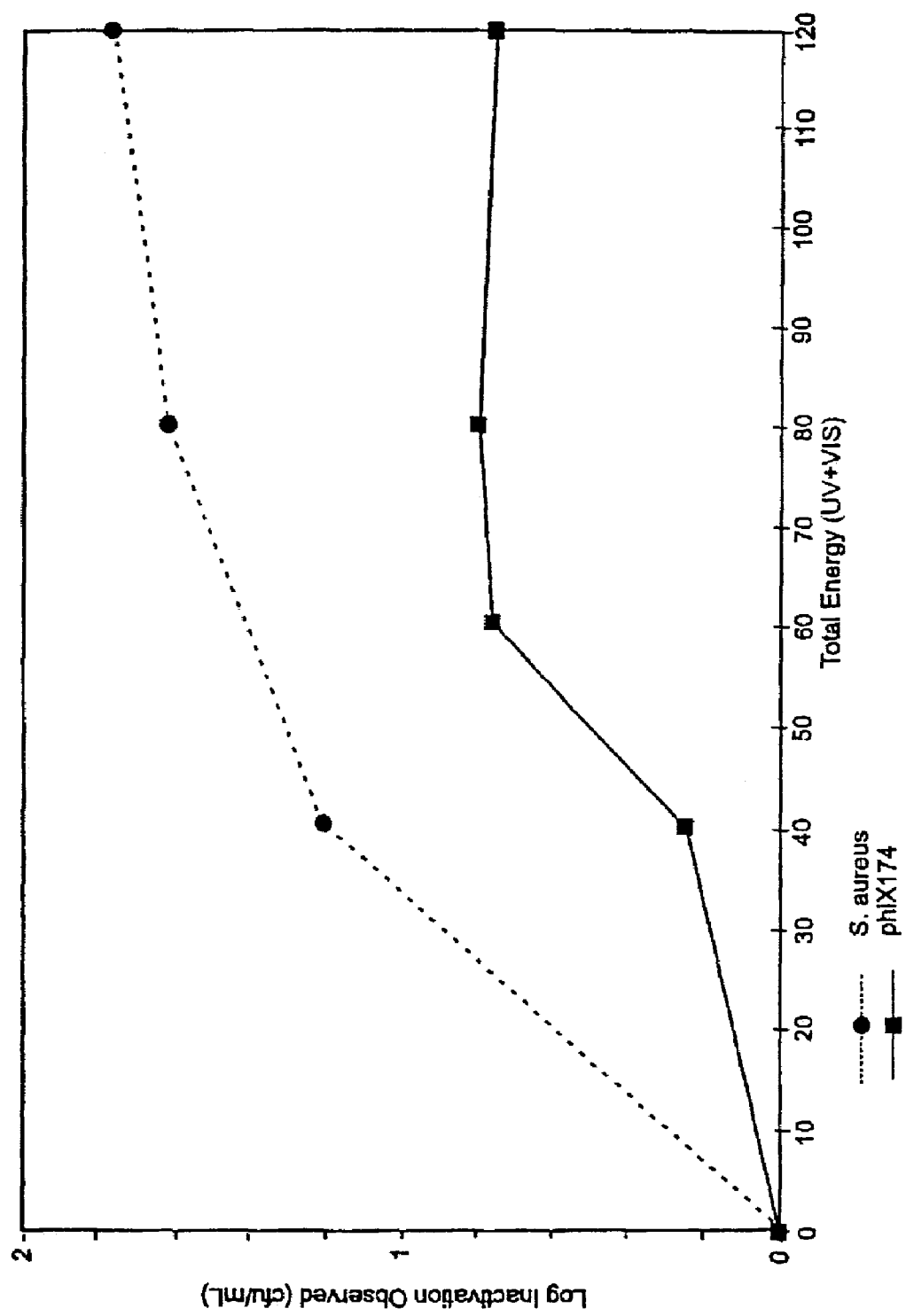
FIG. 13 shows inactivation of *S. aureus* and ΦX174 at varying energies of irradiation using a 50:50 mixture of ultraviolet and visible light.

To platelet concentrates of Example 8 was added 10 µM 7,8-dimethyl-10-ribityl-isoalloxazine. These were spiked with *S. aureus* or ΦX174 and irradiated at varying energies of irradiation with a 50:50 mixture of visible and ultraviolet light. Inactivation results are shown in FIG. 13.

Example 19

Figure 14:
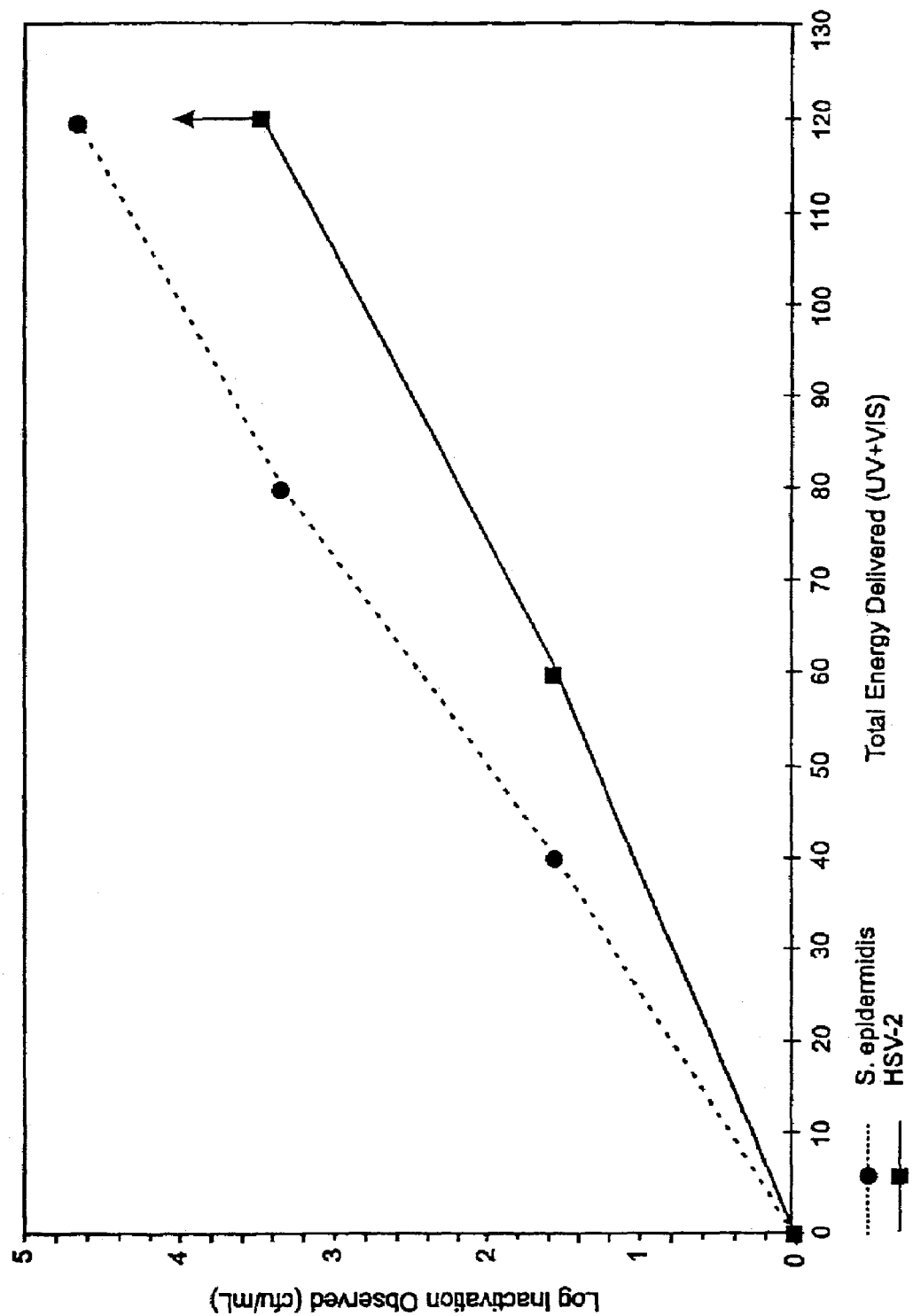
FIG. 14 shows inactivation of *S. epidermidis* and HSV-II at varying energies of irradiation using a 50:50 mixture of ultraviolet and visible light.

The protocol of Example 18 was followed using *S. epidermidis* and HSV-II as the microorganisms. A 50:50 mixture of ultraviolet and visible light was supplied by DYMAX light source. Inactivation results are shown in FIG. 14.

Example 20

Figure 15:
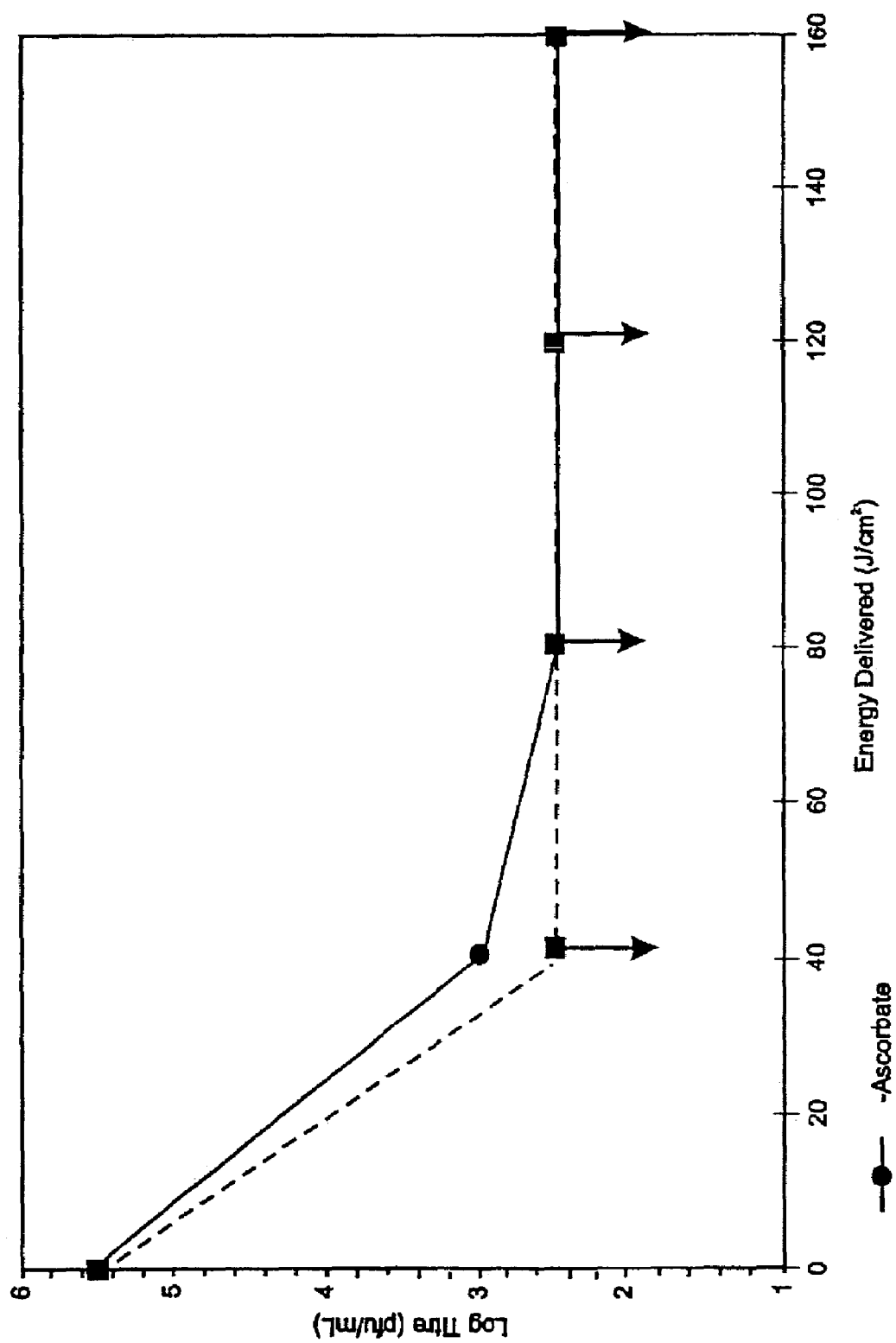
FIG. 15 shows inactivation of HSV2 virus in blood bags agitated and irradiated at varying energy levels.

To platelet concentrate of Example 8 was added 10 µM 7,8-dimethyl-10-ribityl-isoalloxazine in powdered form. Tests with and without added ascorbate were conducted. 150 ml of the test solutions were placed in a Spectra™ blood bag and shaken and exposed to varying energies of irradiation using 50:50 visible:ultraviolet light. After receiving 40 J/cm$^2$, the contents of each bag were transferred to a new bag to avoid errors due to microorganisms which may have remained in the spike port of the bag. Inactivation results are shown in FIG. 15. Downward arrows indicate inactivation to the level it was possible to detect (2.5 log titre).

Example 21

Figure 16:
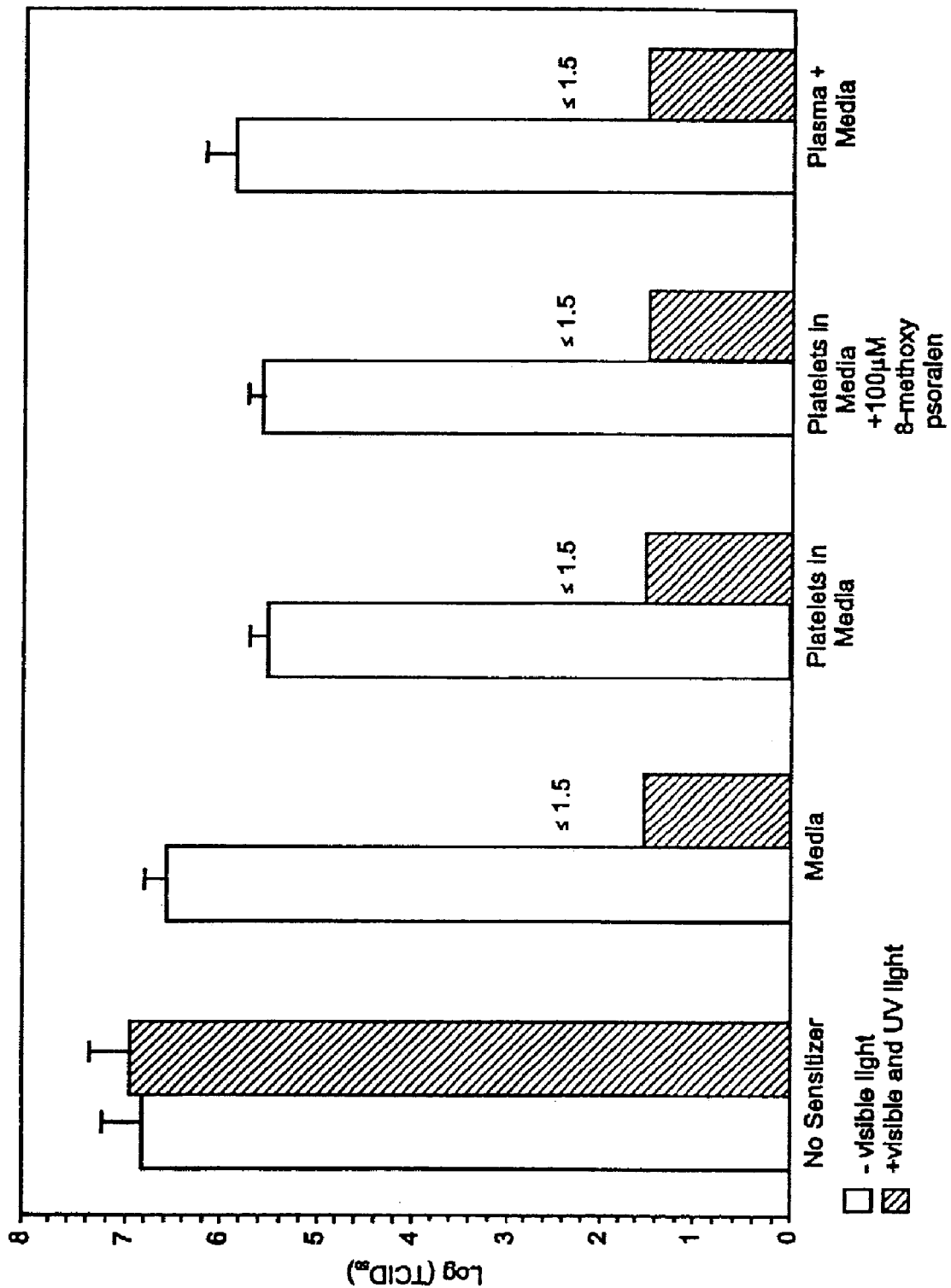
FIG. 16 compares inactivation results for vaccinia virus in various fluids using ultraviolet light alone or 50:50 visible and ultraviolet light.

To platelet concentrate of Example 8 and platelet concentrate in Isolyte S at 30:70 platelet concentrate:Isolyte S, was added 20 µM 7,8-dimethyl-10-ribityl-isoalloxazine. These were spiked with vaccinia virus, a double stranded DNA envelope virus, and exposed to 60 J/cm$^2$ visible light or mixed (50:50) visible and ultraviolet light using a DYMAX 2000 UV light source for 30 minutes. The limit of detection was 1.5 logs. Inactivation results are shown in FIG. 16. Comparisons were done using no photosensitizer, photosensitizer in Isolyte S media alone, platelets in Isolyte S media, platelets in Isolyte S media using 8-methoxy psoralen instead of 7,8-dimethyl-10-ribityl-isoalloxazine, and platelet concentrate in Isolyte media (30:70).

Example 22

Figure 17:
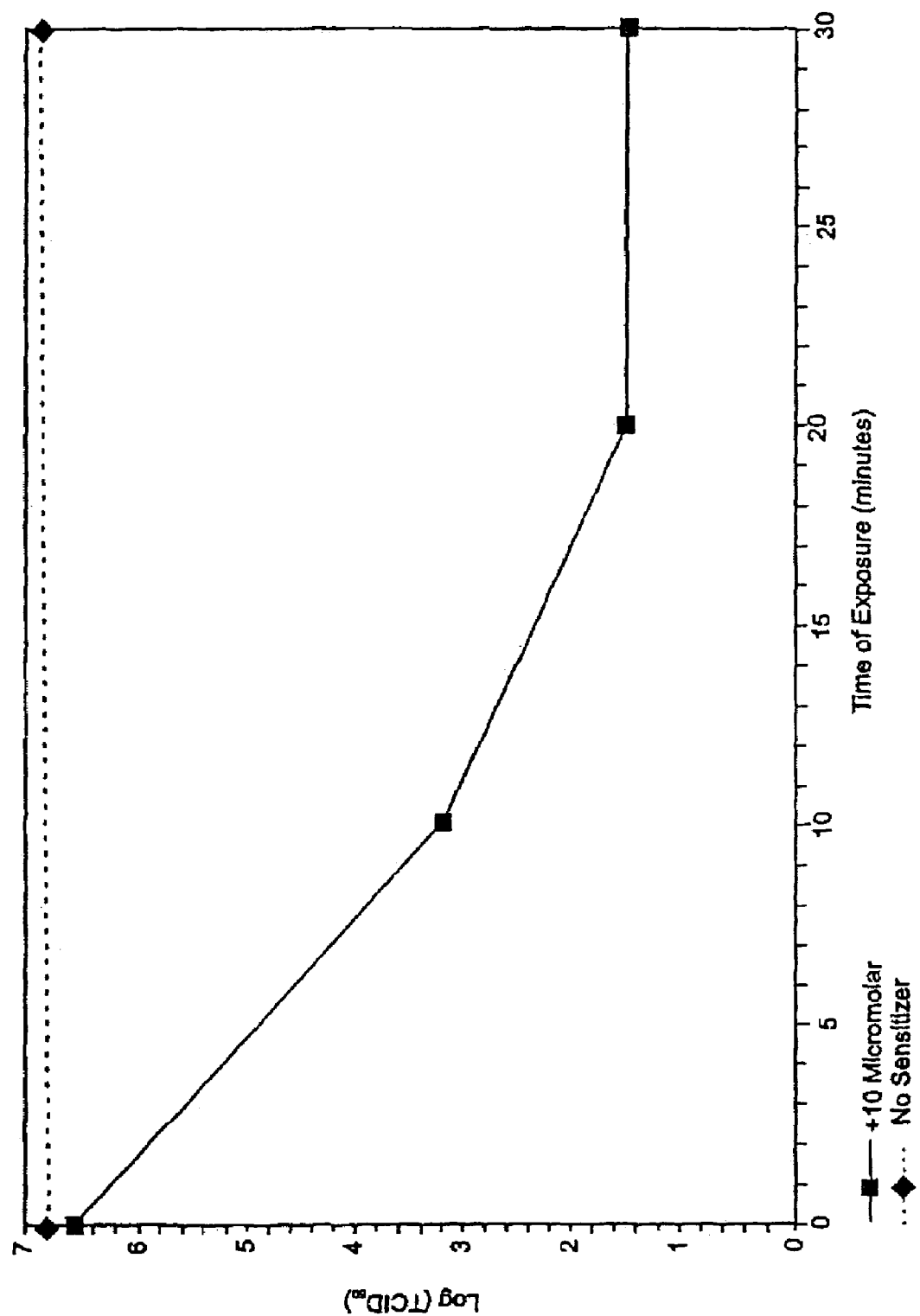
FIG. 17 compares inactivation results with and without sensitizer of vaccinia virus at varying irradiation times.

Samples of platelet concentrate in Isolyte S media 30:70, with and without 10 µM 7,8-dimethyl-10-ribityl-isoalloxazine were spiked with vaccinia virus and irradiated at 60 J/cm$^2$ with 50:50 visible:UV light for varying periods of time and inactivation results compared as shown in FIG. 17.

Example 23

Figure 18:
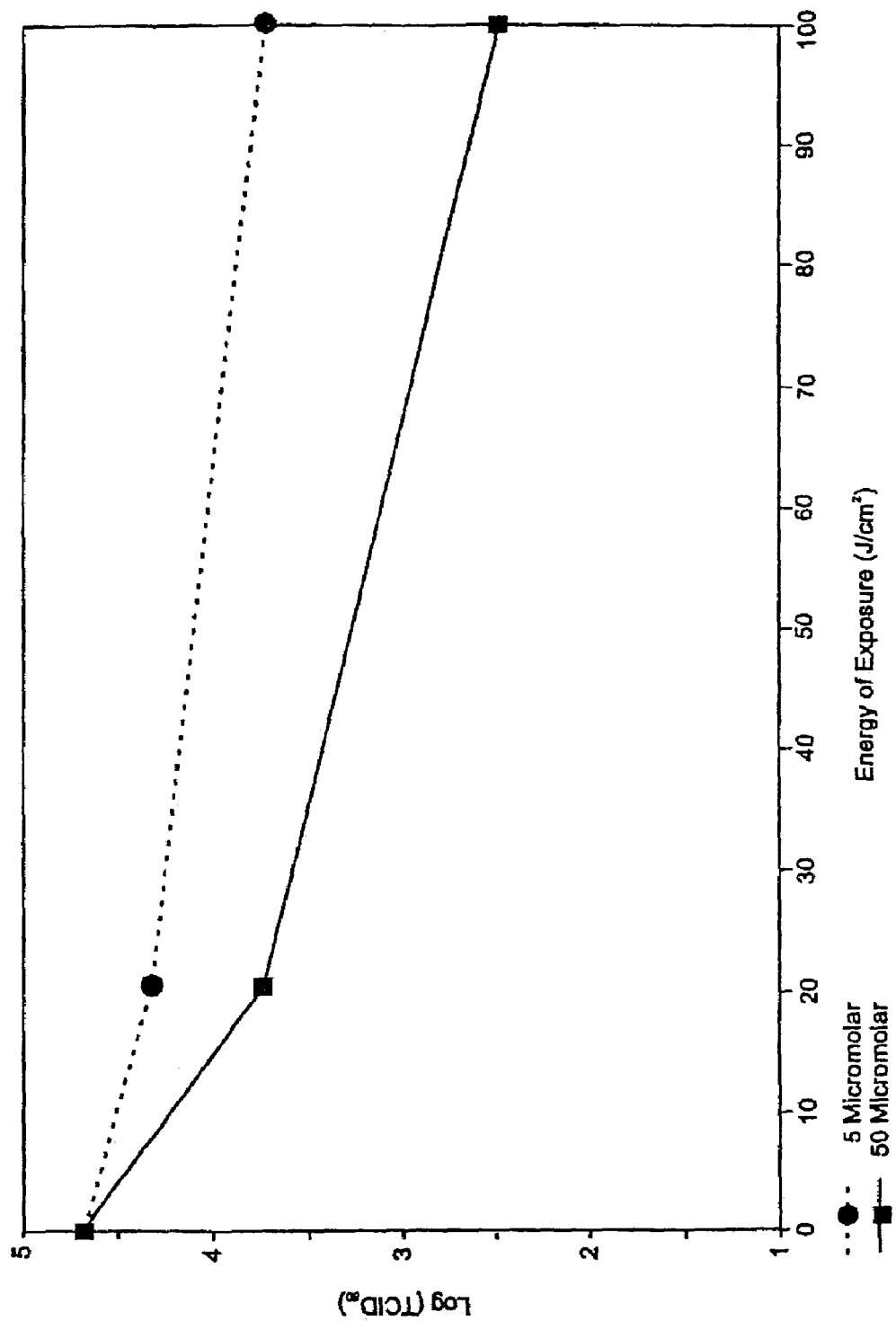
FIG. 18 compares inactivation of extracellular HIV-1 at 5 and 50 μM of photosensitizer and varying irradiation energies.

To samples of platelet concentrate as described in Example 8 were added 5 µM or 50 µM 7,8-dimethy-10-ribityl-isoalloxazine. Samples were spiked with HIV 1. Using the cuvette flow cell shown in FIG. 6, samples were irradiated with 50:50 visible:UV light at varying energies using an EFOS light system. Inactivation results are show in FIG. 18.

Example 24

Figure 19:
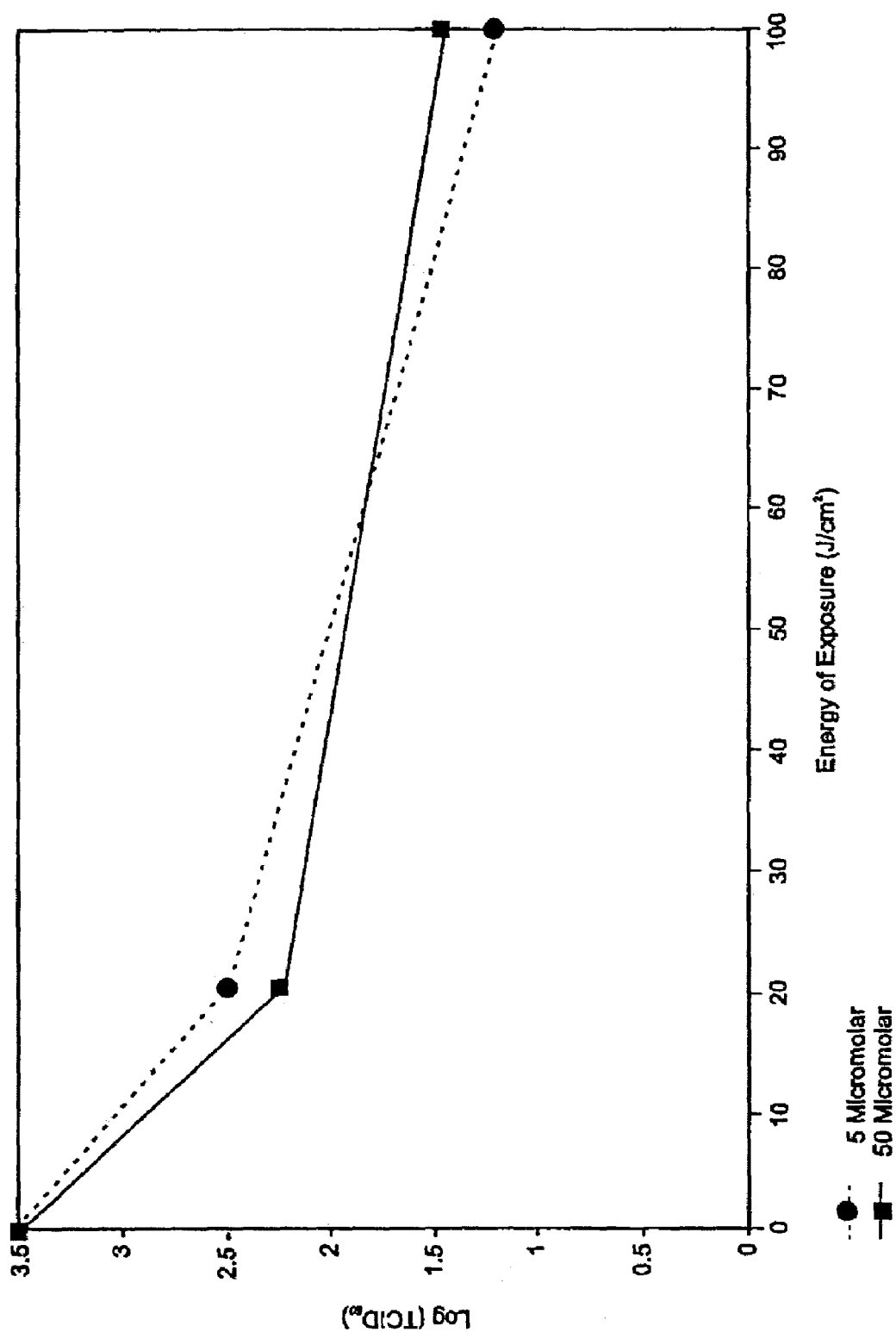
FIG. 19 compares inactivation of intracellular HIV-1 at 5 and 50 μM of photosensitizer and varying irradiation energies.

HIV-infected ACH-2 cells were added to samples of platelet concentrate described in Example 8. 5 or 50 µM of 7,8-dimethyl-10-ribityl-isoalloxazine were added to the samples. The protocol of Example 23 was followed, and inactivation results are shown in FIG. 19. The presence of HIV was assayed by its cytopathic effect on test cells.

Example 25

Figure 20:
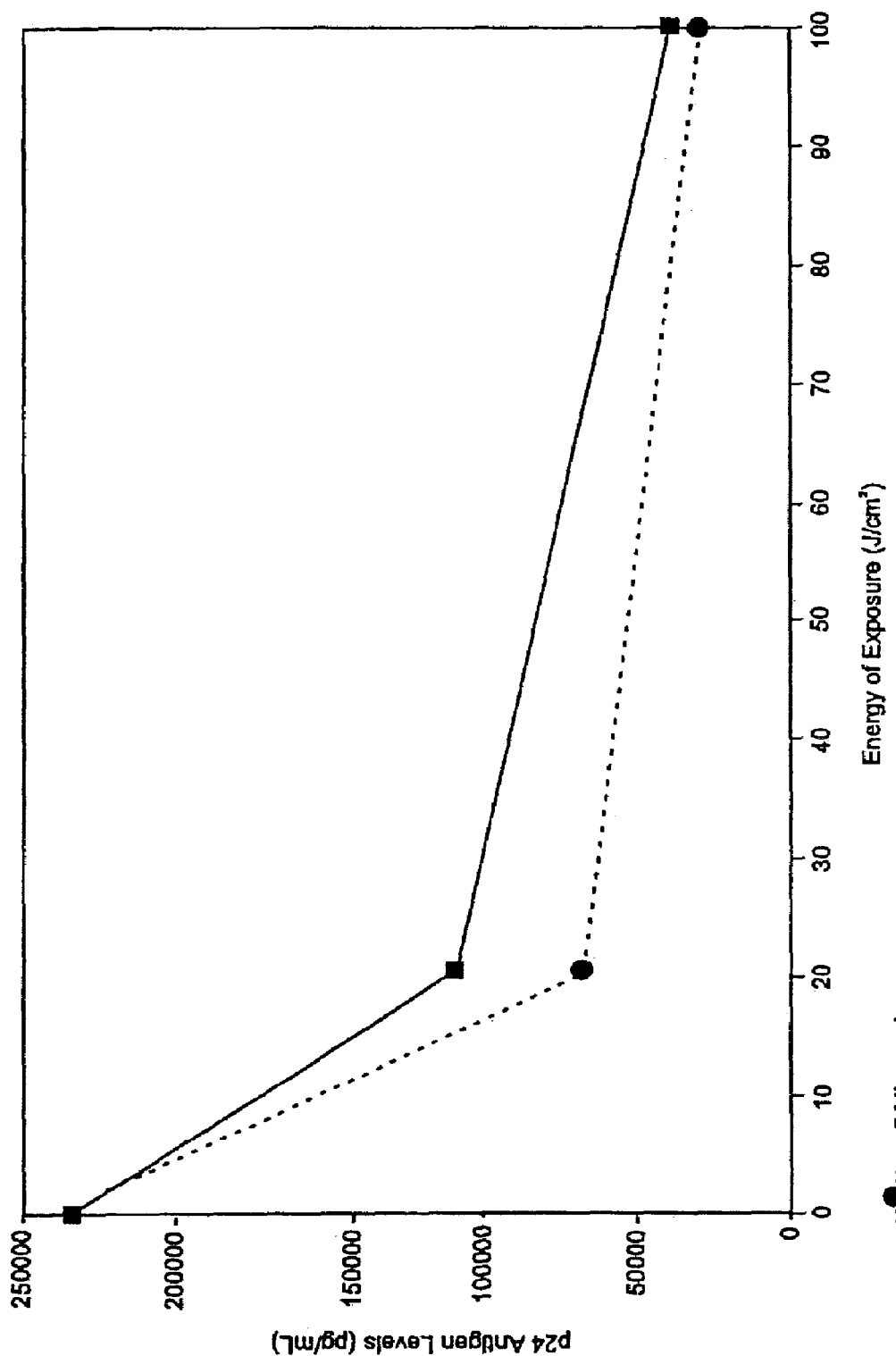
FIG. 20 compares inactivation of intracellular HIV-1 at 5 and 50 μM of photosensitizer and varying irradiation energies, using p24 antigen levels.

The protocol of Example 24 was followed and the presence of HIV assayed by quantifying the level of p24 antigen production. Inactivation results are show in FIG. 20.

Example 26

Figure 21:
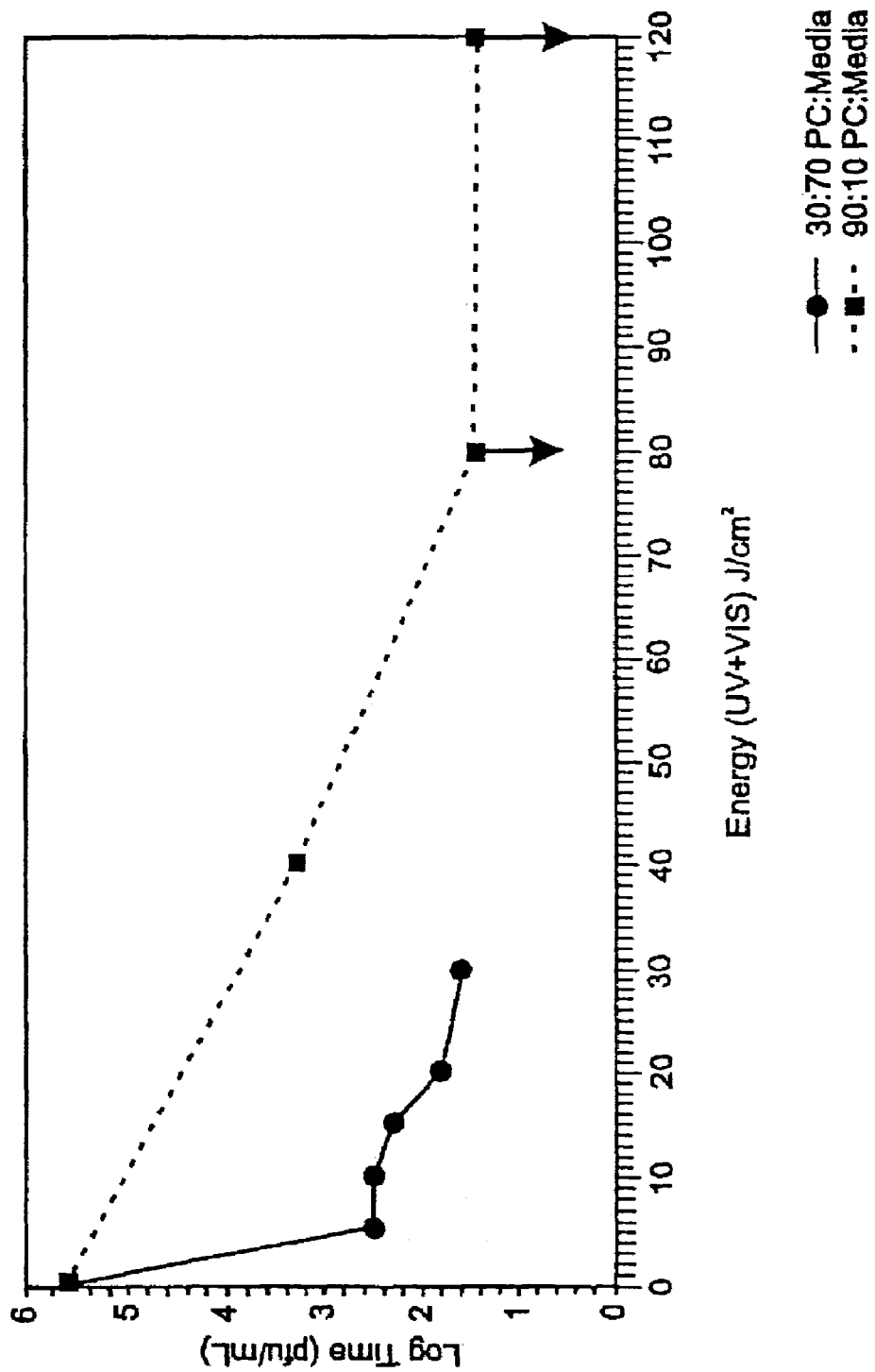
FIG. 21 shows inactivation of HSV-II at varying irradiation levels using platelet concentrate and platelet concentrate in media containing platelet additive solution with ascorbate.

To samples of platelet concentrate as described in Example 8 and media containing 30% platelet concentrate and 70% PASIII™ media were added 6 mM ascorbate and 14 µM 7,8-dimethyl-10-ribityl-isoalloxazine. Samples were spiked with HSV-II. Inactivation results are show in FIG. 21 and Table 11.

TABLE 11

| Time (Minutes) | Energy (UV + VIS) J/cm$^2$ | 30:70 PC:Media log virus titre | Energy (UV + VIS) J/cm$^2$ | 90:10 PC:Media log virus titre |
|---|---|---|---|---|
| 0 | 0 | 5.6 | 0 | 5.6 |
| 1.5 | 5 | 2.5 | 40 | 3.3 |
| 3 | 10 | 2.5 | 80 | 1.5 No Detectable Virus |
| 4.5 | 15 | 2.3 | 120 | 1.5 No Detectable Virus |
| 6 | 20 | 1.8 | | |

TABLE 11-continued

| Time (Minutes) | Energy (UV + VIS) J/cm² | 30:70 PC:Media log virus titre | Energy (UV + VIS) J/cm² | 90:10 PC:Media log virus titre |
|---|---|---|---|---|
| 9 | 30 | 1.6 | | |
| 12 | 40 | | | |
| 24 | 80 | | | |
| 36 | 120 | | | |

It will be readily understood by those skilled in the art that the foregoing description has been for purposes of illustration only and that a number of changes may be made without departing from the scope of the invention. For example, other photosensitizers than those mentioned may be used, preferably photosensitizers which bind to nucleic acid and thereby keep it from replicating, and more preferably those which are not toxic and do not have toxic breakdown products. In addition, equivalent structures to those described herein for constructing a flow-through system for decontamination of fluids using photosensitizers may be readily devised without undue experimentation by those skilled in the art following the teachings hereof.

The invention claimed is:

1. A method of making a vaccine from one or more infectious particles comprising:

inactivating the infectious particles by adding an effective amount of an endogengous isoalloxazine photosensitizer to the one or more infectious particles and exposing the particles to light of a sufficient wavelength to prevent replication of the infectious particles but not substantially destroy the antigenic determinants of the particles; and suspending the inactivated particles in a suspension solution to create a vaccine.

2. The method of claim 1 wherein the infectious particles are viruses.

3. The method of claim 1 wherein the particles are rendered non-infectious by preventing the replication of the infectious particles.

4. A method of making a vaccine containing a live virus comprising the steps of:

adding an effective amount of an endogenous isoalloxazine photosensitizer to the virus and exposing the virus to light of a sufficient wavelength to prevent replication of the live virus but not substantially destroy the antigenic determinants of the virus to create an inactivated live virus; and suspending the inactivated live virus in a suspension solution to create a vaccine.

5. The method of claim 4 wherein the suspension solution is chosen from the group consisting of: saline and water.

6. The method of claim 4 wherein the suspension solution comprises an antibiotic and a preservative.

7. The method of claim 4 wherein the suspension solution comprises an adjuvant.

8. A method for inactivating infectious particles without substantially degrading the antigenic characteristics of the particles, comprising the steps of:

exposing the infectious particles to an inactivation fluid containing at least an endogenous isoalloxazine photosensitizer in an amount sufficient to render the particles substantially non-infectious; and exposing the infectious particles and inactivation fluid to light of a sufficient wavelength and for a sufficient time to render the particles substantially non-infectious but less than that which would result in degradation of the antigenic characteristics of the infectious particles.

9. The step of claim 8 wherein the particles are rendered non-infectious by preventing the replication of the infectious particles.

10. The method of claim 8 wherein the infectious particles are viruses.

11. The method of claim 8 wherein an enhancer is added to the inactivation fluid before the step of exposing the infectious particles and inactivation fluid to light.

* * * * *